(12) United States Patent
Saito et al.

(10) Patent No.: US 10,706,596 B2
(45) Date of Patent: Jul. 7, 2020

(54) X-RAY COMPUTED TOMOGRAPHY APPARATUS AND IMAGE GENERATION APPARATUS

(71) Applicant: Canon Medical Systems Corporation, Otawara-shi (JP)

(72) Inventors: Yasuo Saito, Nasushiobara (JP); Shinsuke Tsukagoshi, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 16/127,779

(22) Filed: Sep. 11, 2018

(65) Prior Publication Data

US 2019/0080491 A1    Mar. 14, 2019

(30) Foreign Application Priority Data

Sep. 12, 2017  (JP) .................................. 2017-174931
Sep. 7, 2018   (JP) .................................. 2018-168189

(51) Int. Cl.
| A61B 6/00 | (2006.01) |
| G06T 11/00 | (2006.01) |
| A61B 6/03 | (2006.01) |
| G16H 30/40 | (2018.01) |
| G16H 30/20 | (2018.01) |

(Continued)

(52) U.S. Cl.
CPC ............ *G06T 11/008* (2013.01); *A61B 6/032* (2013.01); *A61B 6/4085* (2013.01); *A61B 6/463* (2013.01); *A61B 6/465* (2013.01); *G06T 11/005* (2013.01); *G06T 11/006* (2013.01); *G16H 10/60* (2018.01); *G16H 30/20* (2018.01); *G16H 30/40* (2018.01); *G16H 40/63* (2018.01); *G06T 2207/10076* (2013.01); *G06T 2207/10081* (2013.01); *G06T 2211/436* (2013.01)

(58) Field of Classification Search
CPC .......... A61B 6/032; G06T 2207/10081; G06T 11/006
See application file for complete search history.

(56) References Cited

U.S. PATENT DOCUMENTS

2010/0034343 A1* 2/2010 Akino .................. G06T 11/006
                                                                378/15

FOREIGN PATENT DOCUMENTS

| JP | 2007-252898 | 10/2007 |
| JP | 2010-63878 | 3/2010 |
| JP | 2011-92366 | 5/2011 |

* cited by examiner

*Primary Examiner* — Dani Fox
(74) *Attorney, Agent, or Firm* — Oblon, McClelland, Maier & Neustadt, L.L.P.

(57) ABSTRACT

According to one embodiment, an X-ray computed tomography apparatus includes data acquisition circuitry and processing circuitry. The data acquisition circuitry is configured to acquire projection data of a first area and projection data of a second area, the first area being an area where the projection data is complete for one rotation, the second area being an area where the projection data is obtained for an angle smaller than the one rotation. The processing circuitry is configured to perform, for at least part of the first area, reconstruction processing using the projection data corresponding to a partial angle among the projection data and to perform, for the second area, reconstruction processing using the projection data of a smaller acquisition range that is smaller than one rotation.

11 Claims, 23 Drawing Sheets

(51) Int. Cl.
*G16H 40/63* (2018.01)
*G16H 10/60* (2018.01)

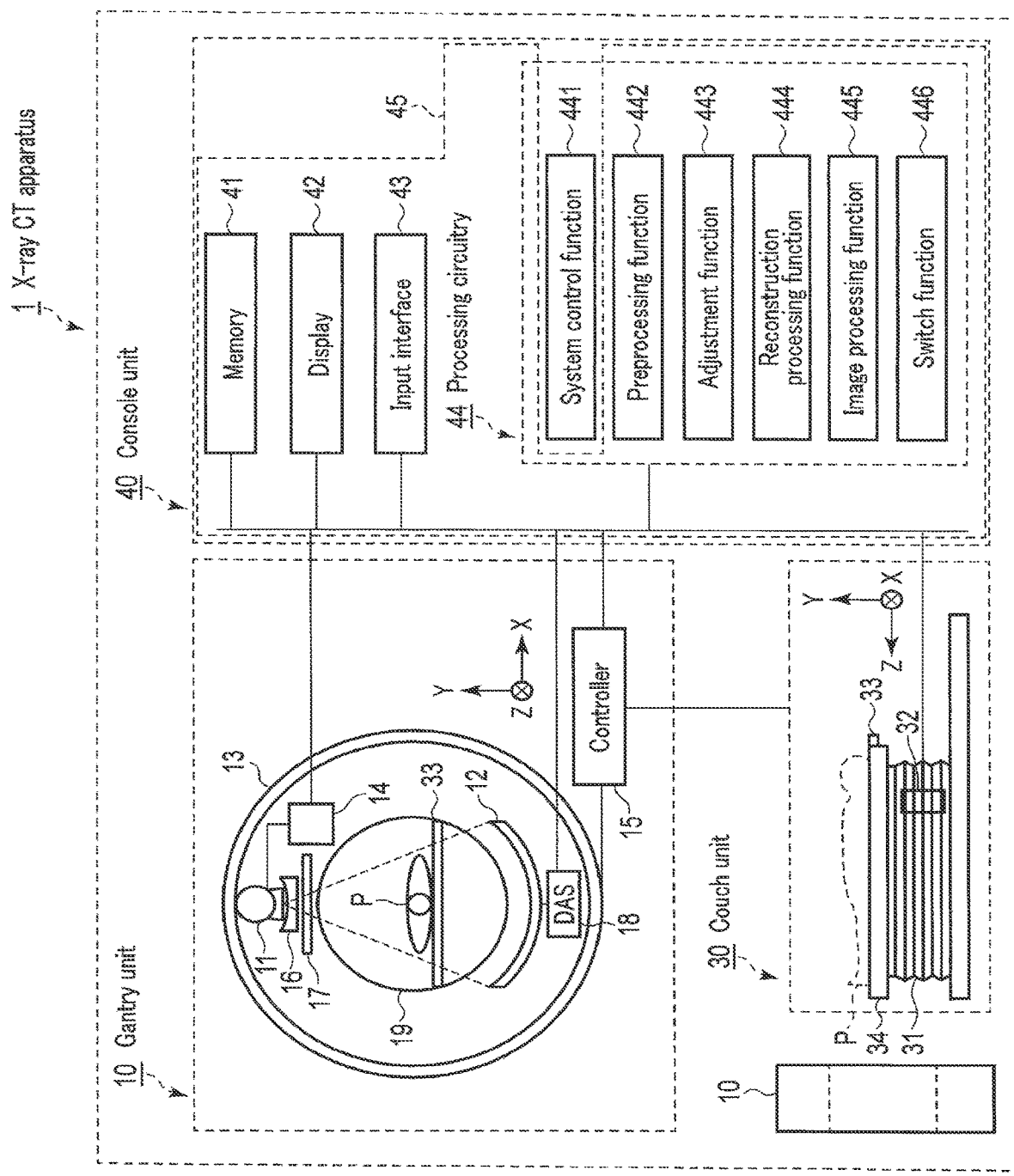
F I G. 1

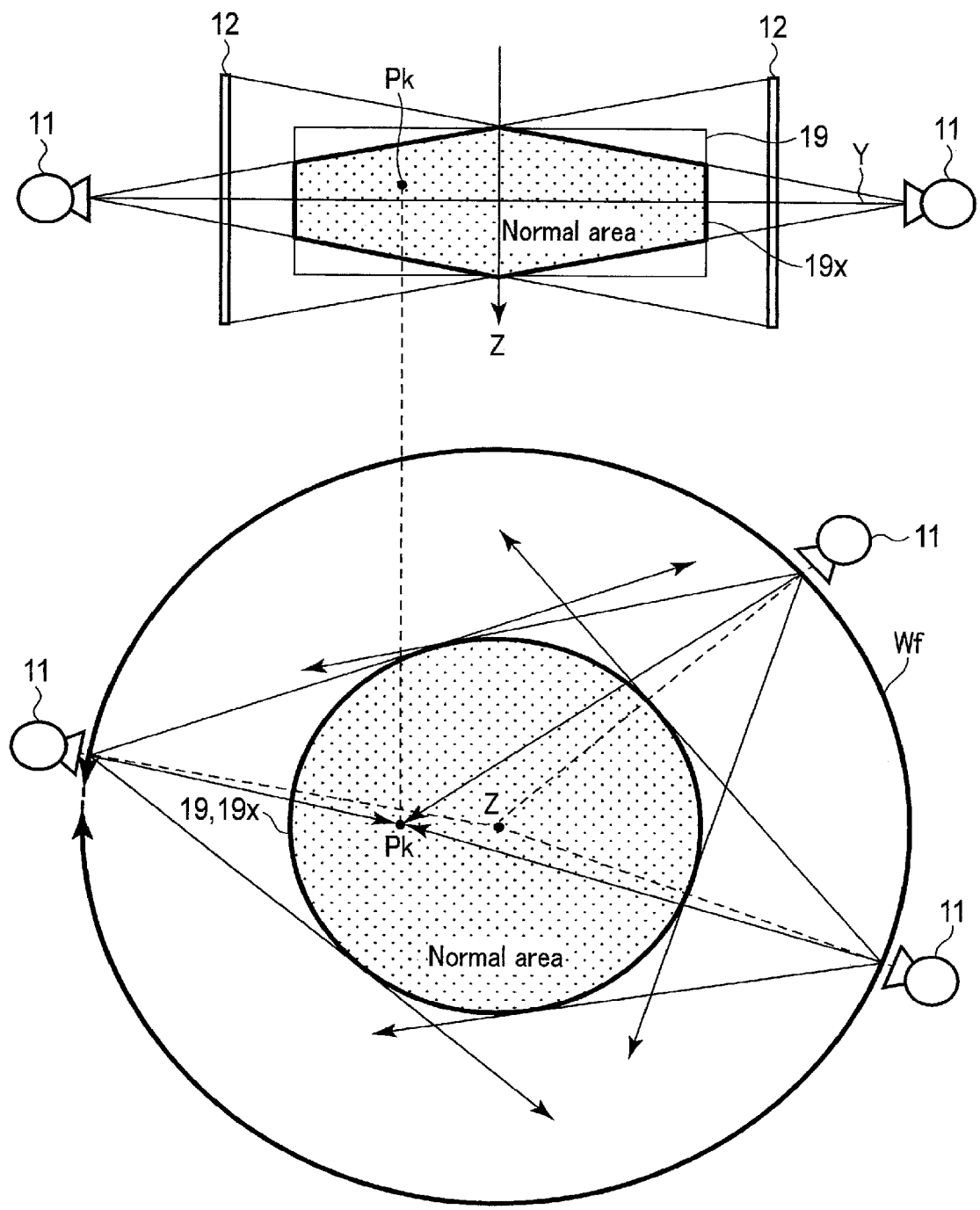
F I G. 2

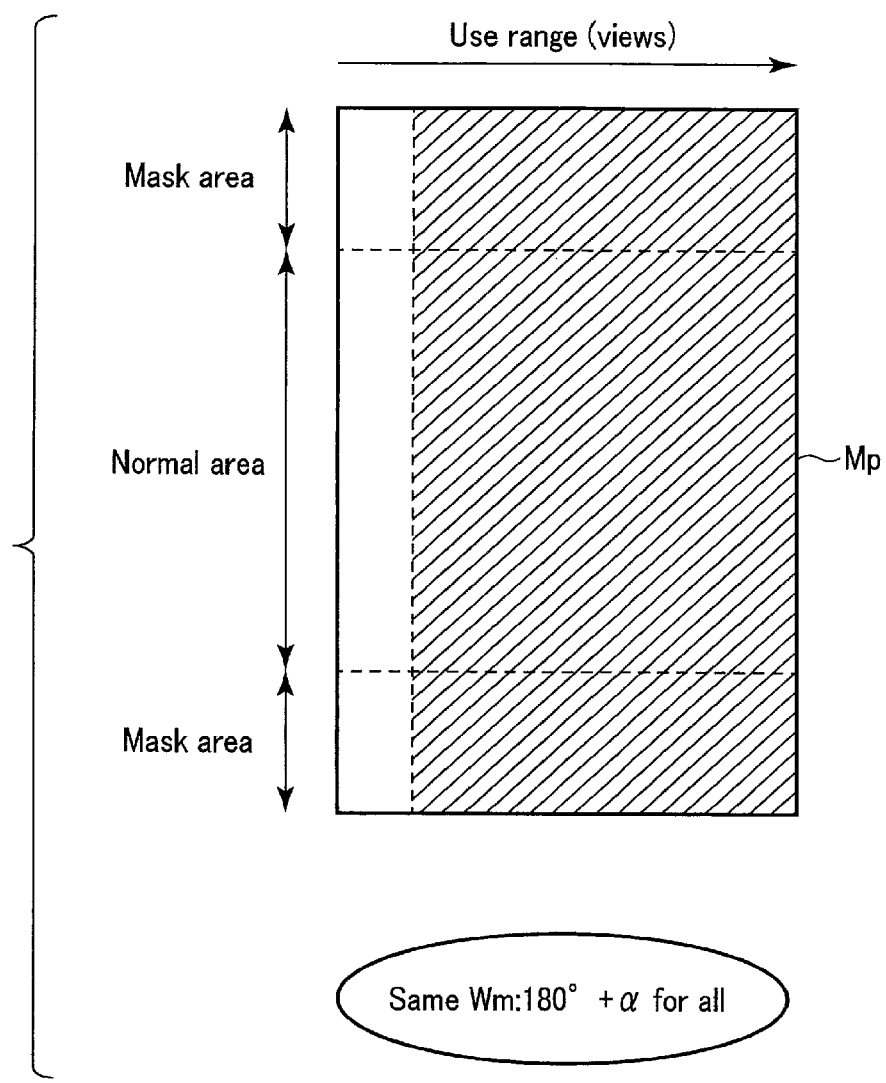
F I G. 10

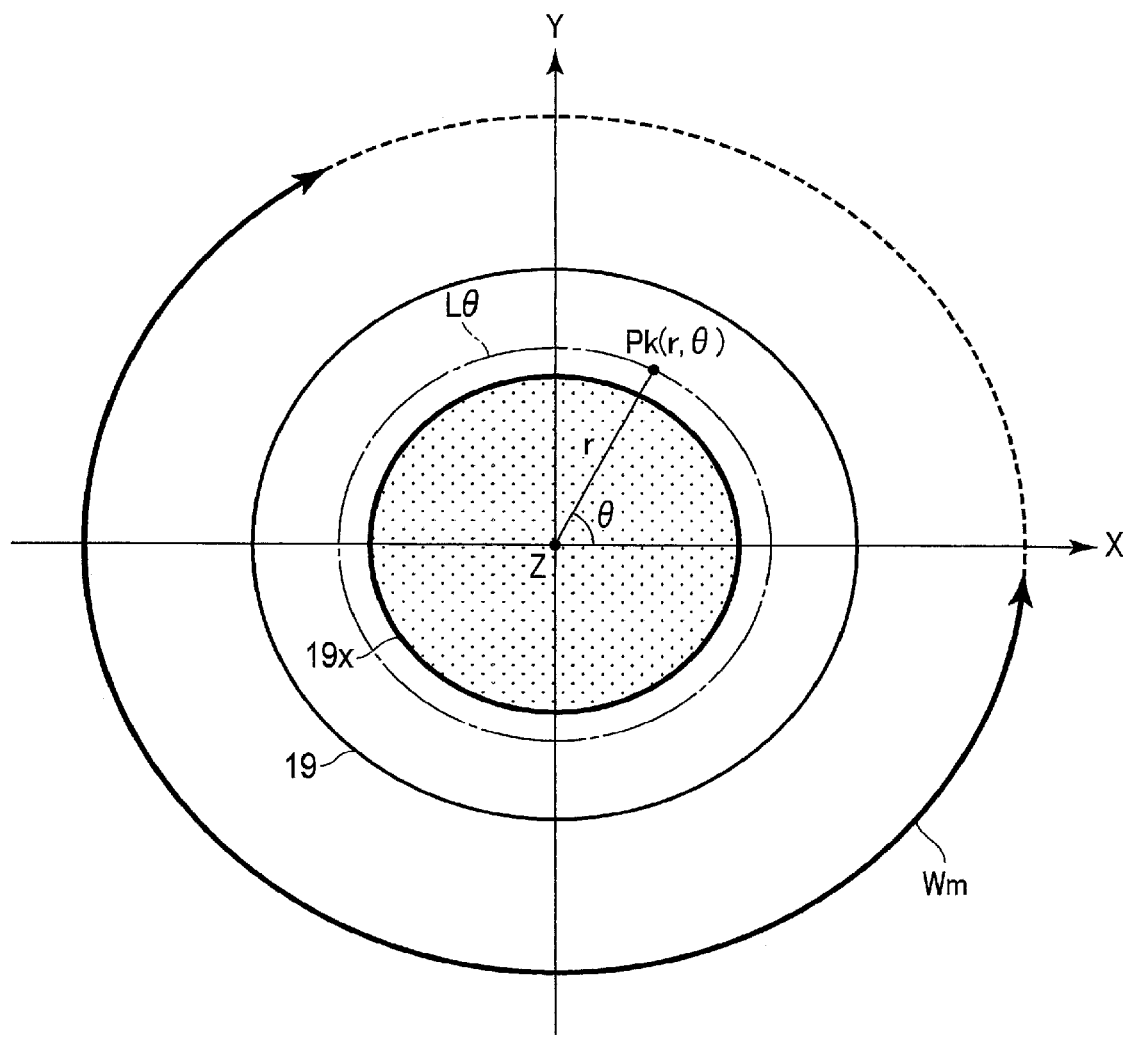
F I G. 22

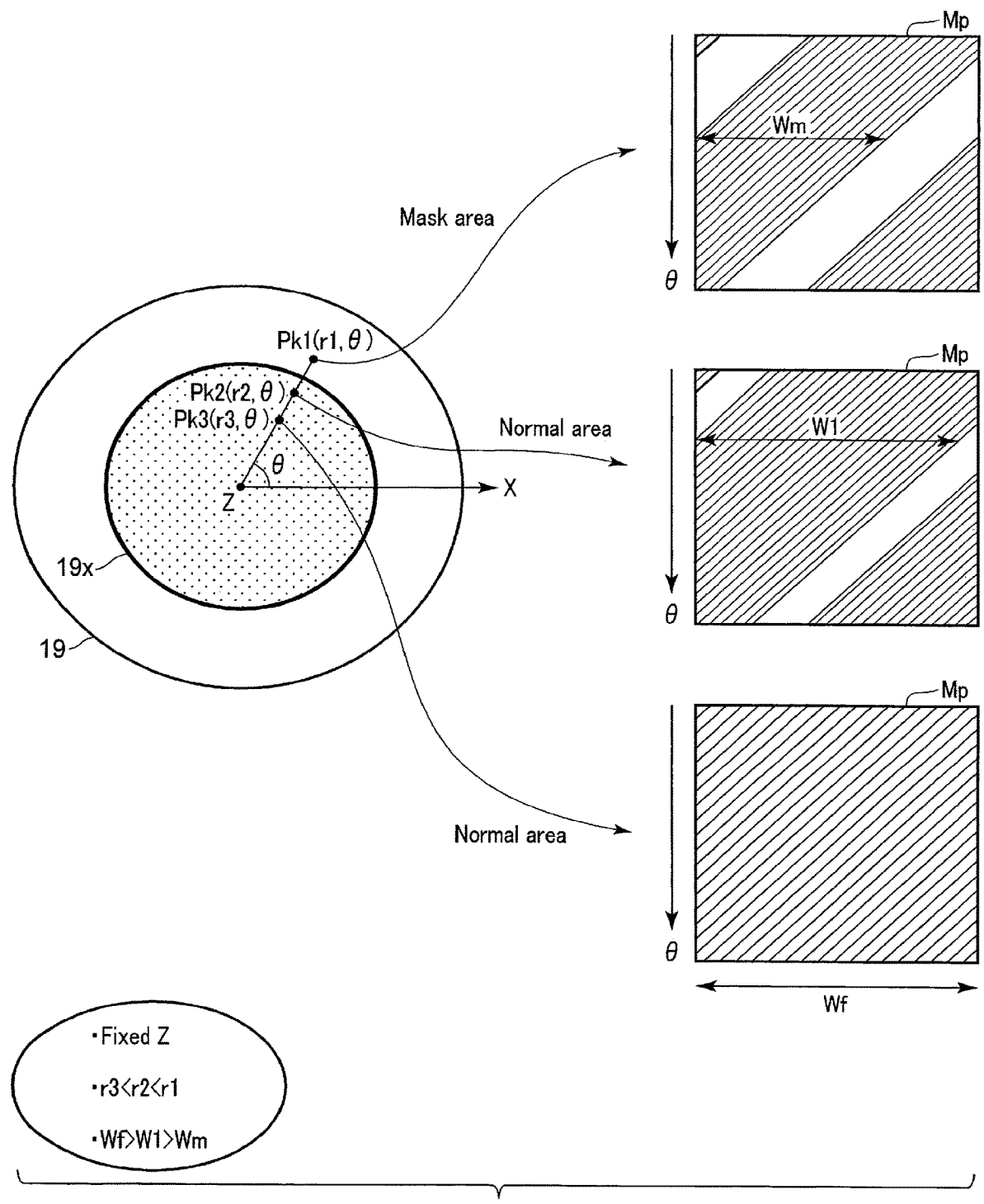
F I G. 24

X-RAY COMPUTED TOMOGRAPHY APPARATUS AND IMAGE GENERATION APPARATUS

CROSS-REFERENCE TO RELATED APPLICATIONS

This application is based upon and claims the benefit of priority from prior Japanese Patent Applications No. 2017-174931, filed on Sep. 12, 2017, and No. 2018-168189, filed on Sep. 7, 2018, the entire contents of all of which are incorporated herein by reference.

FIELD

Embodiments described herein relate generally to an X-ray computed tomography apparatus and an image generation apparatus.

BACKGROUND

Generally, in the field of X-ray computed tomography (CT) apparatuses, an X-ray CT apparatus that includes an X-ray generator to generate cone-beam X-rays and an X-ray detector capable of detecting the X-rays is known. The X-ray CT apparatus of this type can perform volume scanning that causes the X-ray generator to emit X-rays while rotating once along the circular path around a subject, so that projection data for one rotation is acquired from the X-ray detector. The X-ray CT apparatus of this type can also reconstruct, using the one-rotation projection data, a three-dimensional image having an area spreading in the direction of the rotational axis.

However, the range that allows for acquisition of one-rotation projection data is restricted and a field of view (FOV) on the respective axial plane becomes small as the distance from the mid-plane (the central plane defined with respect to the rotational-axis direction) increases. That is, the size of a normal area, where a complete set of one-rotation projection data is available, becomes small. Concurrently, as the normal area becomes small, the size of a mask area—present on both sides of the normal area and where a complete set of one-rotation projection data is not available—becomes large. Note that the mask area is an area which does not enable reconstruction processing with one-rotation projection data, thus resulting in the corresponding area in the resultant image becoming masked.

In this regard, a technique is put into practical use. This technique sees an image of the mask area reconstructed using the projection data acquired from the range smaller than that for one rotation. The technique will also be referred to as "mask area reconstruction". According to this mask area reconstruction, a three-dimensional image, or its tomograms, can be generated by combining reconstructed images of the mask area and the normal area.

As such, the normal area and the mask area differ from each other in the range for acquiring projection data for reconstruction. This range for acquiring projection data corresponds to the range of the rotational angle of a gantry carrying the X-ray generator and the X-ray detector, the range of views, and so on. The difference in the range of the gantry's rotational angle means a difference in the range of time for acquiring projection data, as well as a difference in the averaged acquisition time (average time). Accordingly, a three-dimensional image or a tomogram that combines images of the normal area and the mask area may be understood to be a combination of images differing in the range for acquiring projection data (e.g., average acquisition time).

When the volume scanning is performed on a subject's site, which makes only a small or slow movement, the resultant image does not show a large gap at the boundary between an image of the normal area and an image of the mask area, even though the normal area and the mask area differ from each other in the average acquisition time.

On the other hand, when the volume scanning is performed on a site which is moving largely or quickly (an "actively moving site"), a large gap appears at the boundary between an image of the normal area and an image of the mask area due to the difference between the normal area and the mask area in the average acquisition time. Using a three-dimensional image or its tomograms including such a gap for assessing conditions of adhesion or infiltration to the periphery, etc., involves a risk of degrading assessment accuracy.

The objects intended by the embodiments include reducing the gap appearing at the boundary between an image of the normal area and an image of the mask area when an actively moving site is subject to volume scanning.

BRIEF DESCRIPTION OF THE DRAWINGS

FIG. 1 is a block diagram showing configurations of an X-ray CT apparatus according to a certain embodiment.

FIG. 2 is a schematic diagram for explaining a normal area and an acquisition range in the context of the embodiment.

FIG. 10 is a schematic diagram showing one example of projection data maps corresponding to the respective points on the straight line shown in FIG. 9.

FIG. 22 is a schematic diagram for explaining polar coordinates in the context of a ninth modification of the embodiment.

FIG. 24 is a schematic diagram for explaining adjusted acquisition ranges corresponding to the respective points on circles in the context of the embodiment.

DETAILED DESCRIPTION

Figure 3:
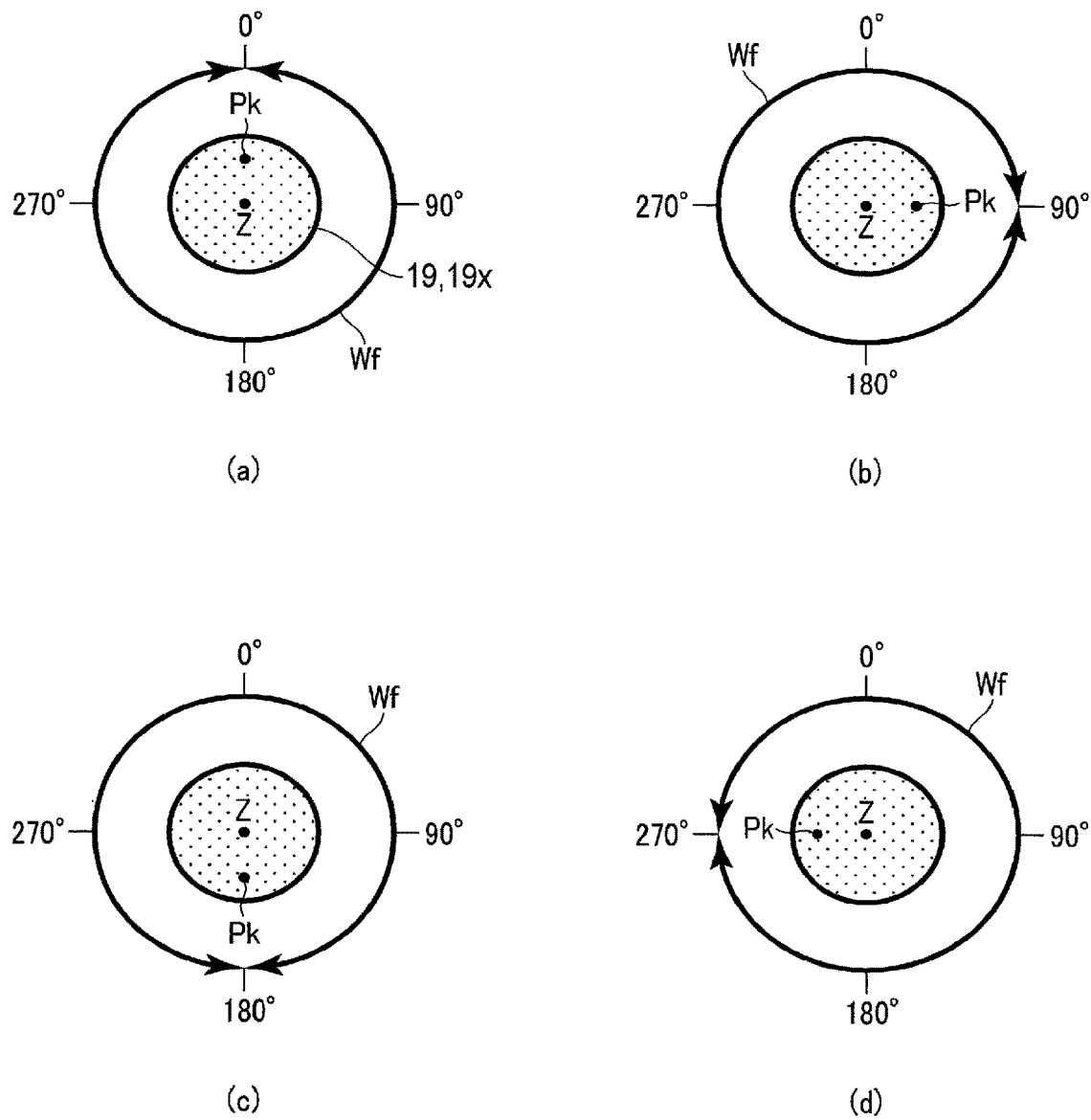
FIG. 3 is a schematic diagram showing a relationship between an angular position of a point Pk in the normal area and an angular position of the midpoint of the acquisition range Wf, in the context of the embodiment.

In general, according to one embodiment, an X-ray computed tomography apparatus includes an X-ray generator, an X-ray detector, data acquisition circuitry, and processing circuitry. The X-ray generator is configured to generate a cone-beam X-ray. The X-ray detector is configured to detect the X-ray from the X-ray generator through a subject. The data acquisition circuitry is configured to acquire projection data of a first area and projection data of a second area via the X-ray detector in conjunction with the X-ray generator performing one rotation around the subject, the first area being an area where the projection data is complete for the one rotation, the second area being an area located on both sides of the first area in a direction along a rotational axis of the X-ray generator and where the projection data is obtained for an angle smaller than the one rotation. The processing circuitry is configured to perform, for at least part of the first area, reconstruction processing using the projection data corresponding to a partial angle among the projection data available for reconstruction and to perform, for the second area, reconstruction processing using the projection data of a smaller acquisition range that is smaller than the one rotation, so that an image of the first area and an image of the second area are obtained.

An X-ray computed tomography (CT) apparatus and an image generation apparatus according to a certain embodiment will be described with reference to the drawings. There are various types of X-ray CT apparatuses, such as a rotate/rotate-type (third-generation CT) which allows an X-ray tube and a detector to rotate around a subject as a unit, and a stationary/rotate-type (fourth-generation CT) which includes many X-ray detecting elements fixed and arrayed in a ring pattern and allows only an X-ray detector to rotate around a subject. The embodiments are applicable to any such type. Also, the image generation apparatus may be provided either inside the X-ray CT apparatus or separately from the X-ray CT apparatus. By way of example, the description will assume that a third-generation CT and an image generation apparatus provided inside the third-generation CT are adopted.

(Configurations of X-Ray CT Apparatus)

FIG. 1 is a block diagram showing configurations of an X-ray CT apparatus according to an embodiment. An X-ray CT apparatus 1 causes an X-ray generator with an X-ray tube 11 to emit X-rays toward a subject P, and detects the X-rays at an X-ray detector 12. The X-ray CT apparatus 1 generates CT images for the subject P based on outputs from the X-ray detector 12. This X-ray CT apparatus 1 may discretionarily be an X-ray CT apparatus that employs multi-slice CTs or multi-detector row CTs (MDCTs) for realizing reconstruction of an area spreading in the rotational-axis direction from the data acquired for one rotation.

The X-ray CT apparatus 1 shown in FIG. 1 includes a gantry unit 10, a couch unit 30, and a console unit 40. The gantry unit 10 is a scanner unit with a configuration to perform X-ray CT imaging for the subject P. The couch unit 30 is a unit for placing thereon a subject of X-ray CT imaging (i.e., the subject P) and moving it to a position where the X-ray CT imaging is carried out. The console unit 40 is a computer for controlling the gantry unit 10.

For example, the gantry unit 10 and the couch unit 30 are arranged in a CT examination room, and the console unit 40 is arranged in a control room that may be adjacent to the CT examination room. The console unit 40 may not have to be arranged in the control room. The console unit 40 may be arranged, for example, together with the gantry unit 10 and the couch unit 30 in the same room. In any case, the gantry unit 10, the couch unit 30, and the console unit 40 are communicably connected to one another either via fixed lines or wirelessly.

The gantry unit 10 includes the X-ray tube 11 and the X-ray detector 12, as well as a rotation frame 13, an X-ray high-voltage device 14, a controller 15, a wedge 16, a collimator 17, and a data acquisition system (DAS) 18.

The X-ray tube 11 is a vacuum tube in which thermal electrons are emitted from a cathode (filament) to an anode (target) using a high-voltage application and a supply of filament current from the X-ray high-voltage device 14. The emitted thermal electrons collide with a focal point on the target, and an energy from this collision converts the thermal electrons into X-rays. The X-ray tube 11 thus generates X-rays for emission toward the subject P from the focal point on the target, having collided with the thermal electrons. The X-rays generated from the X-ray tube 11 are shaped into a cone beam through the collimator 17, and irradiate the subject P. Note that the X-ray tube 11 and the collimator 17 constitute an example of an X-ray generator recited in the claims.

The X-ray detector 12 detects the X-rays having emitted from the X-ray tube 11 and passed through the subject P, and outputs an electrical signal corresponding to the dose of the X-rays to the DAS 18. The X-ray detector 12 includes, for example, multiple rows of X-ray detecting elements. In each of the rows, a plurality of X-ray detecting elements may be arranged in the channel direction along a single arc that centers on the focal point of the X-ray tube. For example, the X-ray detector 12 arranges these multiple rows, each including the X-ray detecting elements in the channel direction, in the slice direction (row direction). Also, the X-ray detector 12 may be an indirect conversion-type detector including, for example, a grid, a scintillator array, and an optical sensor array. The scintillator array includes a plurality of scintillators with scintillator crystals that output light of the photon quantity corresponding to an incident X-ray dose. The grid is provided on the X-ray incident-side face of the scintillator array, and includes an X-ray shielding plate that has a function of absorbing scattered X-rays. The optical sensor array has a converting function to produce electrical signals according to the light amount from the scintillators, and includes, for example, an optical sensor such as a photo-multiplier tube (PMT). Note that the X-ray detector 12 may also be a direct conversion-type detector (semiconductor detector) that includes semiconductor elements for converting incident X-rays into electrical signals. The X-ray detector 12 constitutes an example of an X-ray detector recited in the claims.

The rotation frame 13 supports the X-ray generator and the X-ray detector 12 in such a manner that they can rotate about the rotational axis. More specifically, the rotation frame 13 is a circular frame adapted to support the X-ray tube 11 and the X-ray detector 12 so that they face each other, and to rotate them under the control of the controller 15 as will be discussed. The rotation frame 13 is rotatably supported by a stationary frame (not illustrated) formed of metals, such as aluminum. As a detailed structure, the rotation frame 13 may be connected to the rim of the stationary frame via bearings. The embodiment will assume that: the rotational-axis direction of the rotation frame 13 in its non-tilted state, or the longitudinal direction of a couch top 33 of the couch unit 30, is defined as a Z-axis direction; an axial direction that is orthogonal to the Z-axis direction and horizontal to the floor face is defined as an X-axis direction; and an axial direction that is orthogonal to the Z-axis direction and vertical to the floor face is defined as a Y-axial direction. The rotation frame 13 receives power from a drive mechanism in the controller 15 to rotate about the rotational axis extending in the Z-axis direction (rotational axis Z) at a constant angular velocity. The rotation frame 13 may further carry and support members such as the X-ray high-voltage device 14 and the DAS 18, in addition to the X-ray tube 11 and the X-ray detector 12. The rotation frame 13 of such a configuration is accommodated in a substantially-cylindrical housing with a boar for forming an imaging space. The boar substantially conforms to an FOV 19. The boar has a center axis that coincides with the rotational axis Z of the rotation frame 13. The rotational axis Z of the rotation frame 13 may likewise be referred to as "the rotational axis Z of the X-ray tube 11". Detection data generated by the DAS 18 is transmitted in an optical communication manner from a transmitter including a light-emitting diode (LED) at the rotation frame to a receiver including a photodiode at the non-rotating portion of the gantry unit (e.g., the stationary frame), and transferred to the console unit 40. Note that the manner in which the detection data is sent from the rotation frame to the non-rotating portion of the gantry unit is not limited to such an optical communication. Any technique may be adopted so long as it permits contactless data transmission.

The X-ray high-voltage device 14 includes a high-voltage generator and an X-ray controller. The high-voltage generator includes electric circuitry such as a transformer and a rectifier, and has a function of generating a high voltage to be applied to the X-ray tube 11 and a filament current to be supplied to the X-ray tube 11. The X-ray controller controls output voltages in accordance with the X-rays to be emitted by the X-ray tube 11. The high-voltage generator may adopt a transformer system or an inverter system. The X-ray high-voltage device 14 may be provided in the rotation frame 13 or at a part of the stationary frame (not illustrated) of the gantry unit 10.

The controller 15 includes processing circuitry including a central processing unit (CPU), etc., and the aforementioned drive mechanism which is constituted by a motor, an actuator, etc. The processing circuitry includes, as hardware resources, a processor such as a CPU (as mentioned) or a micro processing unit (MPU), and a memory such as a read only memory (ROM) or a random access memory (RAM). The controller 15 may also be realized by an application specific integrated circuit (ASIC) or a field programmable gate array (FPGA), or other complex programmable logic device (CPLD) or simple programmable logic device (SPLD). The controller 15 controls the X-ray high-voltage device 14, the DAS 18, etc., according to commands given from the console unit 40. The processor reads programs stored in the memory and executes them to realize the intended control. The controller 15 has a further function of controlling operations of the gantry unit 10 and the couch unit 30, in response to input signals given from an input interface furnished at the console unit 40 or the gantry unit 10. For example, the controller 15 controls rotations of the rotation frame 13, tilts of the gantry unit 10, and motions of the couch unit 30 and the couch top 33. The controller 15 realizes the tilting control for the gantry unit 10 by rotating the rotation frame 13 about the axis that is parallel to the X-axis direction, based on tilt angle information input via the input interface furnished at the gantry unit 10. The controller 15 may be provided in the gantry unit 10 or in the console unit 40. The controller 15 may directly incorporate the programs in the processor circuitry, instead of storing them in the memory. In this case, the processor reads the programs incorporated in its circuitry and executes them to realize the control.

The wedge 16 is a filter for adjusting the X-ray dose emitted from the X-ray tube 11. More specifically, the wedge 16 is an attenuation filter which permits the X-rays emitted from the X-ray tube 11 to pass through, so that the X-rays emitted toward the subject P from the X-ray tube 11 exhibit a predetermined distribution. For example, the wedge 16 may be a filter such as a wedge filter or a bow-tie filter prepared by processing aluminum into a shape with a predetermined target angle and a predetermined thickness.

The collimator 17 is constituted by lead strips, etc., and adopted to narrow down the emission range of the X-rays having passed through the wedge 16. The collimator 17 forms a slit using a combination of the multiple lead strips, etc.

The DAS 18 (i.e., a data acquisition system) acquires projection data of a normal area (first area) and projection data of a mask area (second area) via the X-ray detector 12, in conjunction with the X-ray generator rotating around the subject P once. The normal area is an area where the complete projection data for this one rotation is obtained. The mask area is an area located on both sides of the normal area in the direction along the rotational axis of the X-ray generator, and where the projection data for only an angle smaller than one rotation can be obtained. The expression "projection data for one rotation" is replaceable with "projection data of the acquisition range for one rotation". Also, the expression "projection data for an angle smaller than one rotation" is replaceable with "projection data of the acquisition range smaller than one rotation". Specifically, the DAS 18 obtains, for each single view, a digital value indicative of the intensity of X-rays having been attenuated by the subject P. The DAS 18 includes an amplifier for performing amplification processing on the electrical signals output from each X-ray-detecting element of the X-ray detector 12, and an A/D converter for converting the amplified electrical signals into digital signals, so that the DAS 18 generates detection data including digital values represented by the digital signals. The detection data includes a set of a channel number and a row number of the originating X-ray-detecting element, and the digital values of X-ray intensities identified by the view numbers indicative of acquired views. The view number may discretionarily be an order of view acquisition performed (acquisition time), or a number representing the rotational angle of the X-ray tube 11 (e.g., 1 to 1000). The detection data generated by the DAS 18 is sent to the console unit 40 via contactless data transmission circuitry (not illustrated) provided in the gantry unit 10. The DAS 18 constitutes an example of data acquisition circuitry recited in the claims.

The normal area, the mask area, the acquisition range, etc., will be described with reference to FIGS. 2 to 7. The normal area and the mask areas located on respective sides of the normal area together form a cylindrical reconstruction area.

As for the normal area as shown in FIG. 2, upon one rotation of the X-ray tube 11 about the rotational axis Z, projection data of an acquisition range Wf for this one rotation is complete. At the places close to the mid-plane defined with respect to the rotational-axis direction, the FOV 19 that substantially conforms to the boar agrees with an FOV 19x on the respective axial plane. As shown in FIGS. 2 and 3, the angular position corresponding to a point Pk in the normal area and the angular position corresponding to the midpoint of the acquisition range Wf are in the relationship whereby they are opposed to each other with the rotational axis Z therebetween. The point Pk may be referred to as "a target pixel Pk". For example, the angular position represents each point on the circular path along which the X-ray tube 11 rotates about the rotational axis Z once by an angle value ranging from 0° to 360°, assuming that the topmost point on the circular path vertically above the rotational axis Z has an angular position 0°. In FIG. 3(a), the angular position 0° corresponding to the point Pk and the angular position 180° corresponding to the midpoint of the acquisition range wf (0° to 360°) are opposed to each other with the rotational axis Z therebetween. The same can be seen in FIG. 3(b) to (d).

Figure 4:
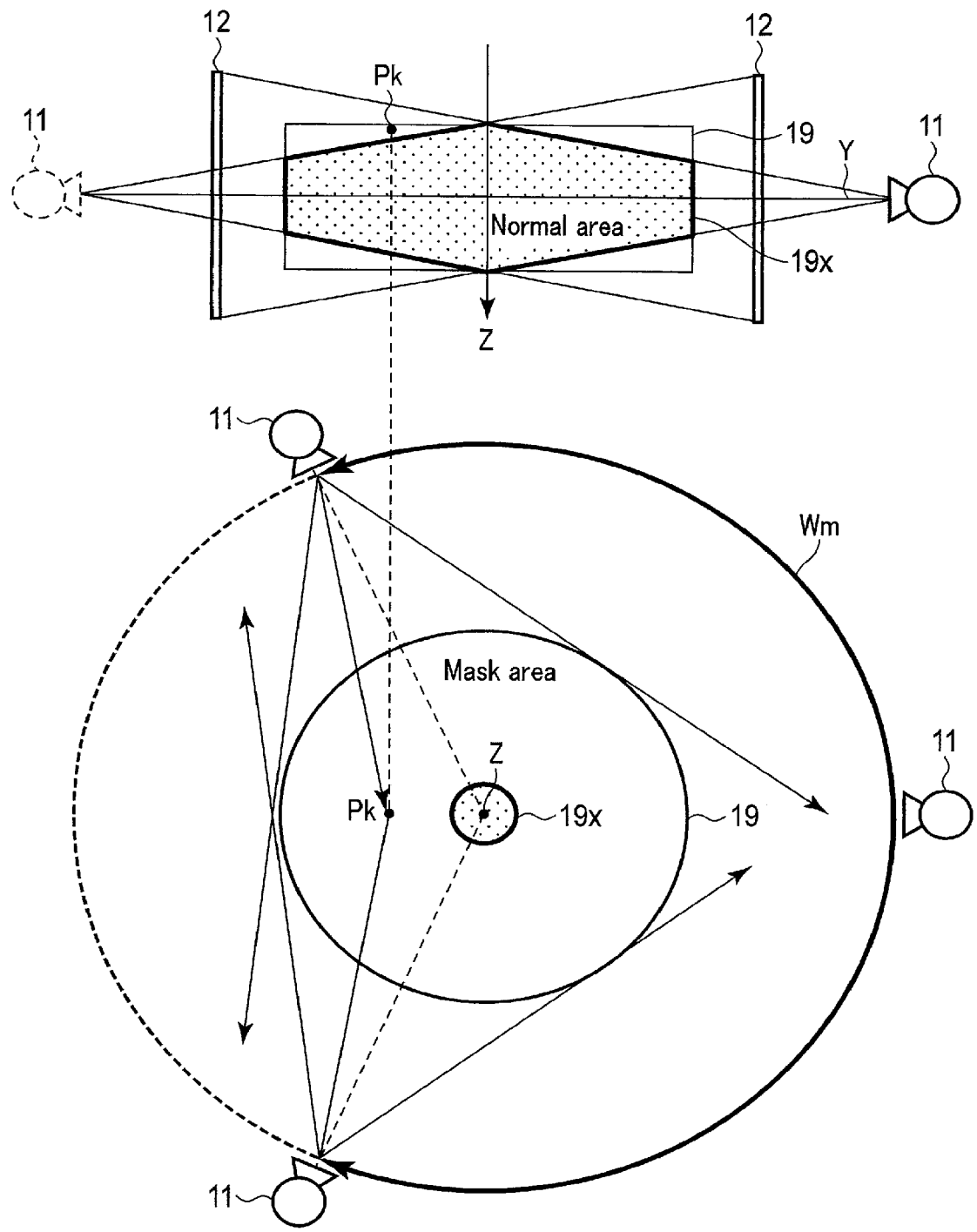
FIG. 4 is a schematic diagram for explaining a mask area and an acquisition range in the context of the embodiment.
Figure 5:
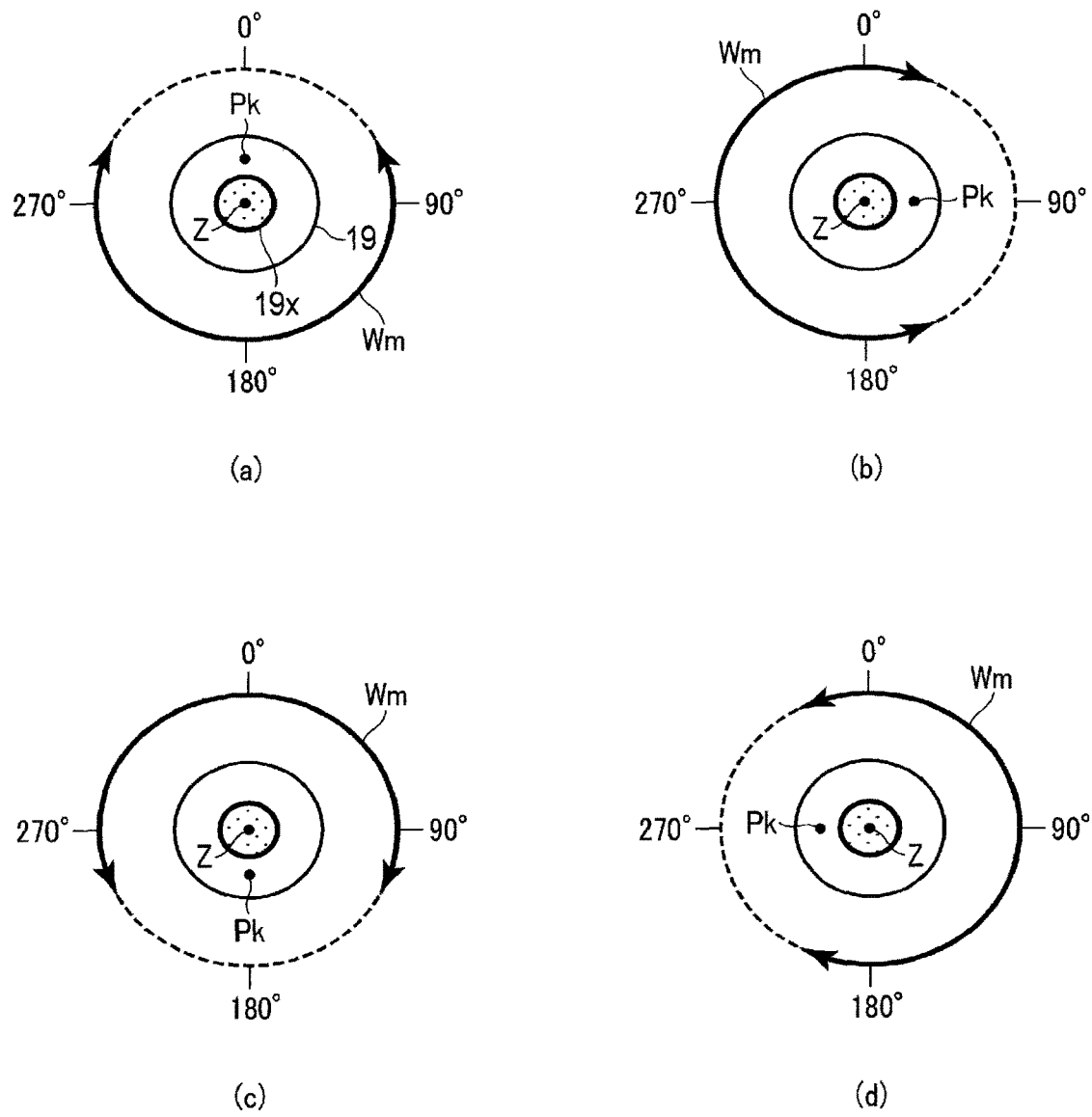
FIG. 5 is a schematic diagram showing a relationship between an angular position of a point Pk in the mask area and an angular position of the midpoint of the acquisition range Wm, in the context of the embodiment.

The mask area is, as shown in FIG. 4, an area located on both sides of the normal area in the direction along the rotational axis Z, and where the projection data of only the acquisition range Wm smaller than one rotation can be obtained. As the distance from the mid-plane defined with respect to the rotational-axis direction increases, the FOV 19x on the axial plane becomes smaller than the FOV 19 that substantially conforms to the boar, and the mask area becomes large. As shown in FIGS. 4 and 5, the angular position corresponding to a point Pk in the mask area and the angular position corresponding to the midpoint of the acquisition range Wm are in the relationship whereby they are opposed to each other with the rotational axis Z therebetween. For example, in FIG. 5(a), the angular position 0° corresponding to the point Pk and the angular position 180° corresponding to the midpoint of the acquisition range Wm ((90°−α/2) to (270°+α/2)) are opposed to each other with the rotational axis Z therebetween. Note that a is a fan angle. The same can be seen in FIG. 5(b) to (d).

Therefore, when the angular position (e.g., 0°) corresponding to the point Pk in the mask area and the angular position (e.g., 0°) corresponding to the point Pk in the normal area are the same, the angular positions (e.g., 180°) corresponding to the respective midpoints of the acquisition ranges Wm and Wf are also the same. Still, the acquisition range Wm associated with the point Pk in the mask area is smaller than the acquisition range for one rotation. The acquisition range Wf associated with the point Pk in the normal area is equal to the acquisition range for one rotation.

Figure 6:
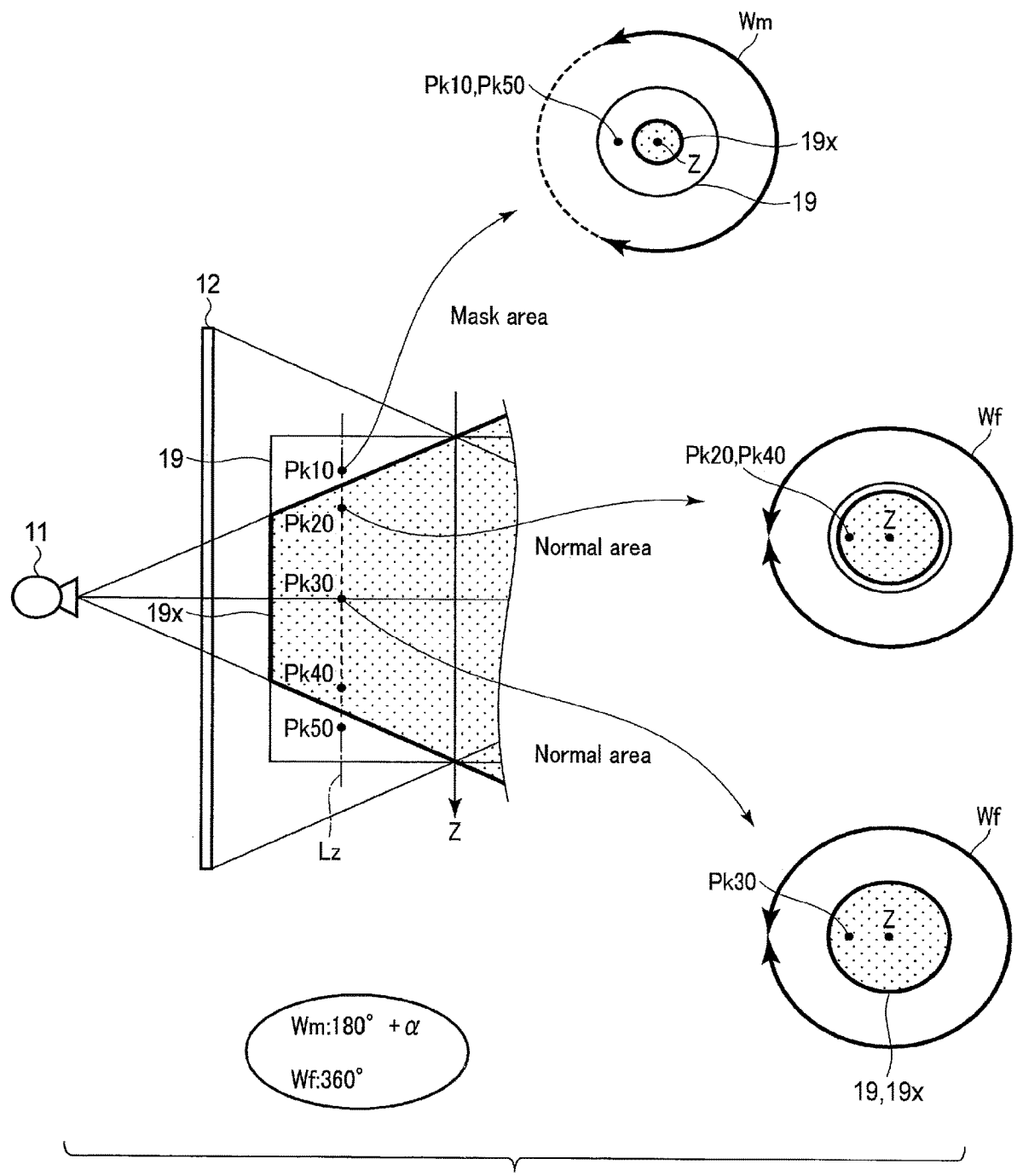
FIG. 6 is a schematic diagram showing acquisition ranges corresponding to the respective points on a straight line in the context of the embodiment.

As such, supposing that there is a straight line Lz as shown in FIG. 6 that penetrates through the mask areas and the normal area in a direction parallel to the direction of the rotational axis Z with constant X-Y coordinate values, multiple points Pk10 to Pk50 positioned on the straight line Lz have the same angular positions based on the straight line Lz, and therefore, the angular positions corresponding to the midpoints of the acquisition ranges Wm and Wf are also the same for the points Pk10 to Pk50. However, the acquisition ranges Wm associated with the respective points Pk10 and Pk50 in the mask areas are smaller than the acquisition range for one rotation (Wm: 180°+α). The acquisition ranges Wf associated with the respective points Pk20, Pk30, and Pk40 in the normal area are equal to the acquisition range for one rotation (Wf: 360°). Note that, for the sake of illustration, the point Pk30 is assumed to be within the normal area and positioned on the mid-plane defined with respect to the rotational-axis direction. The points Pk10 and Pk50 are assumed to be within the respective mask areas, with each being positioned away from the point Pk30 at an equal distance on the straight line Lz. The points Pk20 and Pk40 are assumed to be within the normal area, with each being positioned away from the point Pk30 at an equal distance on the straight line Lz.

Figure 7:
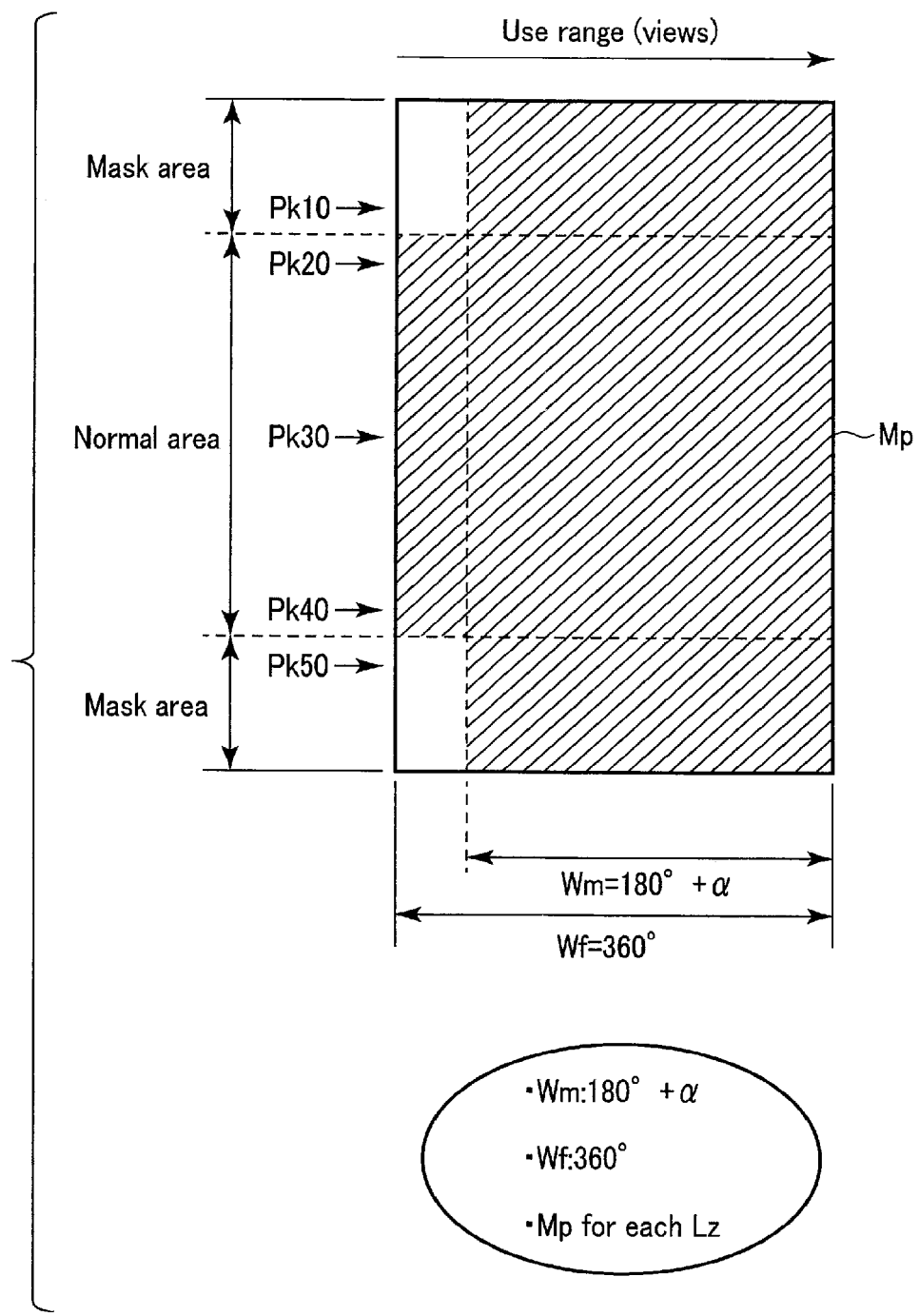
FIG. 7 is a schematic diagram showing one example of projection data maps corresponding to the respective points on the straight line shown in FIG. 6.

The detection data (projection data) for such points Pk on the straight line Lz is stored in a memory 41 (described later) in the form of a projection data map Mp as shown in FIG. 7. This projection data map Mp plots, assuming that the vertical axis represents positions of the respective points Pk on the straight line Lz and the horizontal axis represents views (view numbers), each digital value of the X-ray intensity for the corresponding point Pk at the intersection between the vertical axis and the horizontal axis. The range of views for which the digital values of x-ray intensities are plotted for the position of a given point Pk conforms to the acquisition range or the range for use (in reconstruction) corresponding to the point Pk. For example, the range of views for which the digital values of X-ray intensities are plotted for the position of the point Pk10 located in the mask area conforms to the acquisition range or the use range, Wm, corresponding to the point Pk10. Likewise, the range of views for which the digitals value of X-ray intensities are plotted for the position of the point Pk20 located in the normal area conforms to the acquisition range or the use range, Wf, corresponding to the point Pk20. Note that the horizontal axis of the projection data map Mp is not limited to representation of view numbers, but may also represent rotational angles, acquisition times, etc. Such a projection data map Mp is stored for each straight line Lz.

The couch unit 30 is a unit adapted to carry thereon and move the scanning subject P, and includes a base 31, a couch driver 32, the couch top 33, and a support frame 34.

The base 31 is a housing adapted to support the support frame 34 in such a manner that the support frame 34 can move vertically.

The couch driver 32 is a motor or an actuator adapted to move the couch top 33, on which the subject P is placed, in the longitudinal direction of the couch top 33. The couch driver 32 moves the couch top 33 under the control of the console unit 40 or the controller 15. Also, the couch driver 32 moves the couch top 33 in a direction, for example, orthogonal to the subject P placed on the couch top 33 so that the body axis of the subject P coincides with the center axis of the boar of the rotation frame 13. The couch driver 32 may further move the couch top 33 along the body axis direction of the subject P, according to the X-ray CT imaging performed with the gantry unit 10. To generate power, the couch driver 32 is driven at a rotational rate corresponding to a duty ratio of the drive signals from the controller 15, etc. The couch driver 32 is realized by, for example, a motor such as a direct drive motor or a servo motor.

The couch top 33 is provided on the upper side of the support frame 34, and may be a plate on which the subject P is placed. Note that the couch driver 32 may move not only this couch top 33 but also the support frame 34, in the longitudinal direction of the couch top 33.

The console unit 40 includes the aforementioned memory 41, a display 42, an input interface 43, and processing circuitry 44. The memory 41, the display 42, the input interface 43, and the processing circuitry 44 perform data communications via a bus. The console unit 40 of this configuration, excluding part of the functions of the processing circuitry 44 (i.e., part of a system control function 441 for controlling the gantry unit 10 and the couch unit 30) corresponds to an image generation apparatus 45. In this image generation apparatus 45, the processing circuitry 44 receives the projection data of each of the first area and the second area, which has been acquired by the DAS 18, and performs reconstruction processing with the projection data to obtain images. More specifically, the processing circuitry 44 takes projection data from the DAS 18 or the memory 41, and obtains images by performing reconstruction processing with the projection data corresponding to a partial angle among the one-rotation projection data of at least part of the first area, or with the projection data of the second area. The image generation apparatus 45 of such a configuration may be provided as a discrete apparatus from the X-ray CT apparatus 1, instead of being provided within the X-ray CT apparatus 1 as shown in FIG. 1. The image generation apparatus 45 may also be a server apparatus separate from the X-ray CT apparatus 1. If the image generation apparatus 45 is provided as a separate server, it is possible to omit, for example, the display 42, part of the input interface 43 (such as an operation device including a keyboard) and so on.

The memory 41 is a storage device such as a hard disk drive (HDD), a solid state drive (SSD), or an integrated circuit storage device, adapted to store various information. The memory 41 stores, for example, projection data and reconstructed image data. Other than a HDD, an SSD, or the like, the memory 41 may be a portable storage device such as a compact disc (CD), a digital versatile disc (DVD), or a flash memory, or a driver that reads and writes various information in cooperation with a semiconductor memory device, etc., including a random access memory (RAM). Also, the memory 41 may have its storage region within the X-ray CT apparatus 1 or within an external storage device connected via a network. For example, the memory 41 also stores data of CT images, display images, etc. The memory 41 further stores control programs and multiple projection data maps Mp according to the embodiment, and so on. An instance will be supposed, where a preprocessing function 442 generates multiple projection data maps Mp based on the projection data acquired by the DAS 18. The projection data maps Mp are each indicative of the projection data in association with positions on the straight line Lz extending along the rotational axis Z of the X-ray tube 11, and with acquisition times for the acquisition ranges Wf and Wm or rotational angles of the X-ray tube 11. The rotational angles of the X-ray tube 11 may also be referred to as "rotational angles of the rotation frame 13". After the generation, the preprocessing function 442 writes these projection data maps Mp in the memory 41. The memory 41 thus stores the projection data maps Mp. As a note, it is only required that the projection data maps Mp be prepared prior to adjustment performed by an adjustment function 443, so the projection data maps Mp may be generated at any time, either before or after preprocessing by the preprocessing function 442. Also, while the memory 41 is intended to store projection data, it is not necessarily a requisite for the memory 41 to hold the projection data in the form of a projection data map Mp. In any case, the memory 41 stores the projection data of each of the first area and the second area. The first area is an area where complete one-rotation projection data is acquired from the X-rays generated by the X-ray generator while rotating around a subject once and collected, after passing through the subject, by the data acquisition circuitry via the X-ray detector. The second area is an area located on both sides of the first area in the direction along the rotational axis of the X-ray generator, and where the projection data for only an angle smaller than one rotation can be acquired.

The display 42 displays various information. For example, the display 42 outputs medical images (CT images) generated by the processing circuitry 44, graphical user interfaces (GUIs) for accepting various operations from an operator, and so on. The display 42 may discretionarily be, for example, a liquid crystal display (LCD), a cathode ray tube (CRT) display, an organic electroluminescence display (OELD), a plasma display, or any other display available.

The input interface 43 accepts various input operations from an operator and converts the accepted input operations into electrical signals for output to the processing circuitry 44. For example, the input interface 43 accepts acquisition conditions to apply when acquiring projection data, reconstruction conditions to apply when reconstructing CT images, image-processing conditions to apply when generating post-processed images from CT images, and so on, from an operator. The input interface 43 may discretionarily be, for example, a mouse, a keyboard, a trackball, switches, buttons, a joystick, a touch pad, and a touch-panel display. Note that the input interface 43 in this embodiment is not limited to a member with a physical operational component such as a mouse, a keyboard, a trackball, switches, buttons, a joystick, a touch pad, and a touch-panel display. That is, the examples of the input interface 43 also include processing circuitry for electrical signals that receives an electrical signal corresponding to an input operation from an external input device separate from the apparatus, and outputs the electrical signal to the processing circuitry 44.

The processing circuitry 44 takes total control of the X-ray CT apparatus 1 according to the electrical signals of the input operations, output from the input interface 43. For example, the processing circuitry 44 includes, as hardware resources, a processor such as a CPU, an MPU, and a graphics processing unit (GPU), and a memory such as a ROM and a RAM. The processing circuitry 44 implements the system control function 441, the preprocessing function 442, and the adjustment function 443, as well as a reconstruction processing function 444, an image processing function 445, a switch function 446, etc., using a processor adapted to run a program loaded into the memory.

The system control function 441 controls each function of the processing circuitry 44 based on the input operations accepted from an operator via the input interface 43. More specifically, the system control function 441 reads the control program stored in the memory 41, loads it into the memory in the processing circuitry 44, and controls each component of the X-ray CT apparatus 1 according to the loaded control program. For example, the processing circuitry 44 controls each function of the processing circuitry 44 based on the input operations accepted from an operator via the input interface 43.

The preprocessing function 442 performs preprocessing, such as logarithmic conversion, offset correction, inter-channel sensitivity correction, and beam hardening correction, on the detection data output from the DAS 18 to produce preprocessed data. Note that data before the preprocessing (detection data) and data after the preprocessing may be generically referred to as "projection data". The preprocessing function 442 also generates multiple projection data maps Mp as discussed above, based on, for example, projection data before the preprocessing, and writes these projection data maps Mp in the memory 41. As illustrated in, for example, FIG. 8, the projection data map is a map that shows the projection data in association with positions on the straight line Lz extending along the rotational axis Z of the X-ray tube 11 (that is, positions in the mask areas and the normal area), and with acquisition times for the acquisition ranges Wf and Wm or rotational angles of the X-ray tube 11—that is, use range (views). The projection data maps Mp generated by the preprocessing function 442 each involve a large difference between the acquisition range Wm for the mask area and the acquisition range Wf for the normal area, and this difference in acquisition range causes a gap in the reconstructed image of an actively moving site. Note that the projection data may not have to be managed in the form of the projection data maps Mp.

Figure 9:
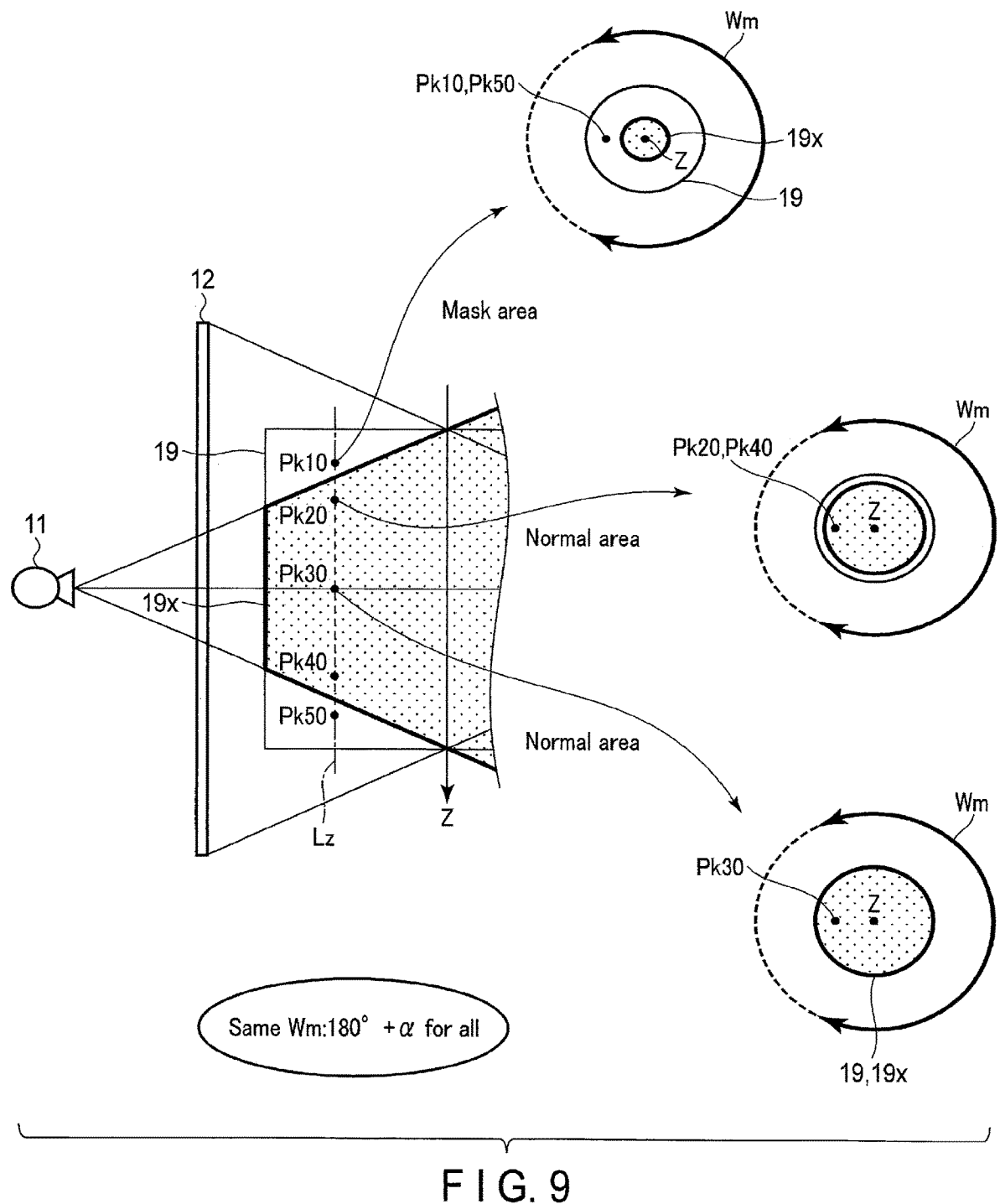
FIG. 9 is a schematic diagram showing adjusted acquisition ranges corresponding to the respective points on a straight line in the context of the embodiment.

As for the adjustment function 443, in order for the reconstruction processing to use projection data corresponding to a partial angle among the one-rotation projection data, the adjustment function 443 adjusts such a partial angle for at least part of the normal area (the first area). For example, the adjustment function 443 adjusts the use range used for reconstructing an image of the normal area within the acquisition range Wf for the projection data of the normal area. Here, the use range of projection data corresponds to the angle (the view number) for the projection data. Note that the purpose would be served if the use range used for reconstructing an image of the normal area exists between the acquisition range Wf for the projection data of the normal area and the acquisition range Wm for the projection data of the mask area. The acquisition range Wm for the projection data of the mask area coincides with the use range used for reconstructing an image of the mask area. The adjustment function 443 may also adjust the use range used for reconstructing an image of the normal area so that it has the same range as the acquisition range Wm for the mask area, which is smaller than one rotation. For example, referring to FIG. 9, in the normal area as shown on the left side, the use range among the acquisition range Wf is adjusted to have the same range as the acquisition range Wm for the mask area as shown on the right side. Accordingly, the projection data after this adjustment does not create a difference between the use range Wm for the mask area and the use range Wm for also the normal area, and will not cause a gap at the boundary between these areas in the reconstructed image of even an actively moving site.

When an image of the mask area (the second area) is reconstructed using the projection data that is less than the 360° view acquired by one rotation, the adjustment function 443 as above adjusts the projection-data acquisition ranges (acquisition time range, rotational angle range, view number range, etc.) for use in the reconstruction for the normal area (where the 360° projection data has been acquired). The adjustment function 443 may perform this adjustment with reference to, for example, the projection-data acquisition ranges for use in the reconstruction for the mask area, or according to an operation by an operator. For example, the adjustment function 443 may set the projection-data acquisition range for use in the reconstruction for the normal area to be the same as the acquisition range for the mask area. The adjustment of the adjustment function 443 may also allow the projection data corresponding to a part (partial angle) of the angle of one rotation to be used in order to keep the continuity near the boundary between the normal area and the mask area. For example, the adjustment function 443 may adjust the projection-data acquisition ranges for use in the reconstruction for the normal area, so that they are consecutively connected at the boundary between the normal area and the mask area and create continuous changes within a predetermined range in the normal area. The adjustment function 443 may cause the continuous changes of the acquisition ranges according to an operation by an operator via a user interface UI.

The reconstruction processing function 444 generates CT image data by subjecting the projection data generated by the preprocessing function 442, or the projection data of the use range adjusted by the adjustment function 443, to the reconstruction processing adopting filtered back-projection technique, iterative approximation reconstruction technique, short reconstruction technique, etc. The short reconstruction technique may also be referred to as "pixel-based sector reconstruction (PBS)". The reconstruction processing function 444 includes a function of reconstructing an image of the normal area using the projection data from the use range adjusted by the adjustment function 443, as well as reconstructing an image of the mask area using the projection data from the smaller acquisition range. The reconstruction processing function 444 may also include a function of reconstructing an image of the normal area based on the multiple projection data maps with use ranges adjusted by the adjustment function 443. The CT image data is indicative of the spatial distribution of CT values for the subject P.

Note that the reconstruction processing function 444 may include the adjustment function 443. In this case, the reconstruction processing function 444 obtains images by performing, for at least part of the normal area (first area), the reconstruction processing with the projection data corresponding to a partial angle among the projection data available for reconstruction; and by performing, for the mask area (the second area), the reconstruction processing with the projection data of the acquisition range smaller than one rotation. The reconstruction processing function 444 as such may separately perform the reconstruction processing for the part of the normal area and for the mask area for obtaining images. The reconstruction processing function 444 may concurrently perform the reconstruction processing for the part of the normal area and for the mask area for obtaining images, as well.

The image processing function 445 converts the CT image data generated by the reconstruction processing function 444 into tomographic data of a given section, three-dimensional image data, etc., through the known technique, based on the input operations accepted from an operator via the input interface 43. The tomographic data, the three-dimensional image data, etc., after the conversion are displayed by the display 42. As the known technique for conversion, for example, the three-dimensional image processing such as volume rendering, surface rendering, image-value projective processing, multi-planer reconstruction (MPR) processing, and curved MPR processing may be discretionarily adopted.

The switch function 446 switches the adjustment function 443 between an on state and an off state. The switch function 446 may take either a manual configuration or an automatic configuration, or may be omitted. With the manual configuration, the switch function 446 switches the adjustment function 443 for adjusting partial angles (adjustment processing) between the on state and the off state according to an operator's operation. With the automatic configuration, the switch function 446 may, for example, switch the adjustment function 443 from the off state to the on state, in response to images of the normal area and the mask area being obtained by the reconstruction processing and based on a gap between the obtained images. Additionally, the switch function 446 may also switch the adjustment function 443 to the on state or to the off state based on the presence or size of the gap between these images.

Note that the system control function 441, the preprocessing function 442, the adjustment function 443, the reconstruction processing function 444, the image processing function 445, and the switch function 446 may be implemented by the processing circuitry 44 as a single circuit board, or may be implemented by the processing circuitry 44 constituted by multiple circuit boards, respectively. Similarly, while the description has assumed that the console unit 40 executes multiple functions as a single console, the console unit 40 may be constituted by separate consoles to execute the multiple functions. Furthermore, while the description has assumed that the image generation apparatus 45 executes multiple functions as a single apparatus, the image generation apparatus 45 may be constituted by separate apparatuses to execute the multiple functions.

Now, the operations of the X-ray CT apparatus and the image generation apparatus configured as above will be described with reference to the flowchart of FIG. 11. The description will focus on the operations after completion of the tasks such as positioning by scanogram imaging, setting of imaging conditions, activation of gantry rotation, etc. Also, the description will assume an instance where the adjustment function 443 is in the off state at the start of step ST10, although the adjustment function 443 may be in either the on or the off state then.

The X-ray CT apparatus 1 performs volume scanning while the X-ray generator including the X-ray tube 11 and the collimator 17 is rotating (step ST10). At this time, the DAS 18 acquires the projection data of the normal area and the projection data of the mask area via the X-ray detector 12, upon the X-ray generator performing one rotation around the subject P. The normal area is an area where the complete projection data for this one rotation is obtained. The mask area is an area located on both sides of the normal area and where the projection data of only the acquisition range smaller than one rotation is obtained.

Figure 8:
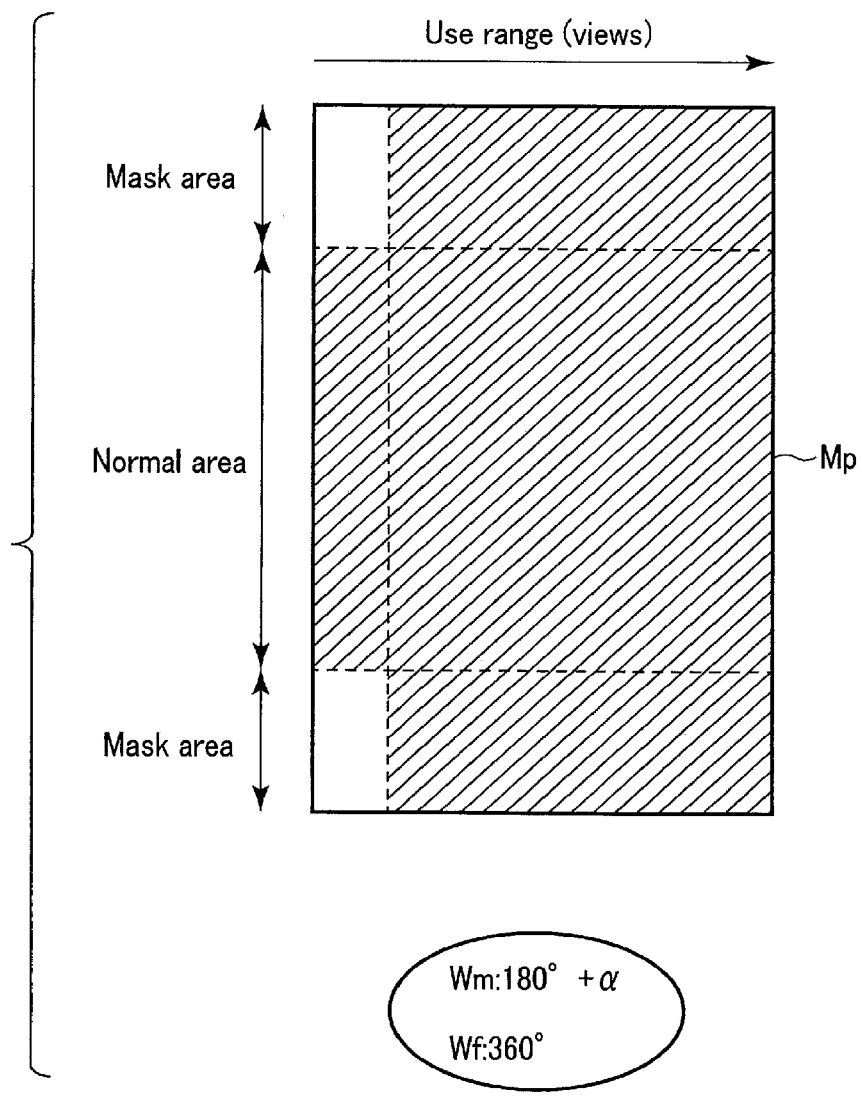
FIG. 8 is a schematic diagram showing one example of projection data maps in the context of the embodiment.

The preprocessing function 442 of the image generation apparatus 45 generates preprocessed data using the detection data output from the DAS 18. Also, the preprocessing function 442 may generate multiple projection data maps Mp as shown in FIG. 8, based on the projection data after the preprocessing. As noted above, the adjustment function 443 is in the off state and makes no action here.

The reconstruction processing function 444 performs the reconstruction processing on the projection data generated by the preprocessing function 442 to generate CT image data (step ST20). This CT image data includes the image data for the normal area and the image data for the mask area.

The image processing function 445 converts the CT image data generated in step ST20 into tomographic data of a given section, three-dimensional image data, etc. The tomographic data, the three-dimensional image data, etc., after the conversion are displayed by the display 42 (step ST30).

In this context, it will be supposed that the displayed data (e.g., tomographic data) shows a gap at the boundary between the mask area and the normal area.

It will also be supposed that in step ST10, the acquisition of one-rotation projection data is started at time "10 (hr):00 (min):00 (sec):00" and completed at time "10:00:00:30". In this example, the range of the acquisition time for the one-rotation projection data is time "10:00:00:00 to 10:00:00:30", and the average acquisition time is 10:00:00:15. On the other hand, it will be supposed that, among the one-rotation projection data, projection data for ⅔ rotation is used as the projection data smaller than one rotation. In a plain example, the range of the acquisition time for the ⅔ rotation projection data is time "10:00:00:00 to 10:00:00:20", and the average acquisition time is 10:00:00:10. As such, when the acquisition ranges for projection data differ, the average acquisition times for the projection data also differ. Consequently, when the volume scanning is performed on an actively moving site, a gap appears at the boundary between the images of the normal area and the mask area since the average acquisition times for the normal area and mask area are different.

At this time, the switch function 446 switches the adjustment function 443 to the on state according to, for example, an operator's operation (step ST40).

The adjustment function 443 adjusts the use range used for reconstructing the image of the normal area, within the acquisition range Wf for the projection data of the normal area (step ST50). The adjustment function 443 here adjusts the use range used for reconstructing the image of the normal area so that, for example, it has the same range as the smaller acquisition range Wm for the mask area as shown in FIG. 10.

The reconstruction processing function 444 reconstructs the image of the normal area using the projection data from this adjusted use range, and also reconstructs the image of the mask area using the projection data from the smaller acquisition range (step ST60).

Thereafter, the image processing function 445 converts the images reconstructed in step ST60 into tomographic data of a given section, three-dimensional image data, etc. The tomographic data, the three-dimensional image data, etc., after the conversion are displayed by the display 42 (step ST70).

According to the embodiment described, the data acquisition circuitry acquires projection data of a first area and projection data of a second area via the X-ray detector, in conjunction with the X-ray generator rotating around a subject once. The first area is an area where the complete projection data for this one rotation is obtained. The second area is an area located on both sides of the first area in the direction along the rotational axis of the X-ray generator, and where the projection data for only an angle smaller than one rotation can be obtained. The processing circuitry obtains images by performing, for at least part of the first area, reconstruction processing using the projection data corresponding to a partial angle among the projection data available for reconstruction and by performing, for the second area, reconstruction processing using the projection data of the acquisition range smaller than one rotation. Both the X-ray CT apparatus 1 and the image generation apparatus 45 may be configured in this manner.

Therefore, the embodiment can reduce the gap appearing at the boundary between the image of the mask area (second area) and the image of the normal area (first area) when an actively moving site is subject to volume scanning. The embodiment can be likewise applied to the cases of four-dimensional scans, in which volume scanning is performed repeatedly at the same position and multiple sets of three-dimensional image data are reconstructed in time series. Such multiple sets of three-dimensional image data may differ from each other in time phase, or may have time phases synchronized with each other.

Also, according to the embodiment, the projection data corresponding to a partial angle, as described above, is used in order to keep the continuity near the boundary between the first area and the second area. With this configuration, the embodiment can remove the gap appearing at the boundary.

Moreover, according to the embodiment, the processing circuitry switches the on/off state of the adjustment processing for adjusting a partial angle, in accordance with an operation by an operator. Therefore, for example, if a four-dimensional scanning operation results in a gap, the adjustment processing is switched on so that the reconstruction can be tried again. Note that if the adjustment processing is always on, the time consistency of volume data will be lost since, normally in the volume data, the projection data used for the mask area and the projection data used for the normal area differ in time range. For example, an instance will be supposed where an ordinary site that is not actively moving is subject to volume scanning, and the average acquisition time for the mask area is 10:00:00:10 and the average acquisition time for the normal area is 10:00:00:15. In this instance, if the use range used for reconstructing an image of the normal area is constantly adjusted to become the same range as the smaller acquisition range for the mask area, the average acquisition time for the whole of the volume data will be shifted to conform to the average acquisition time for the mask area. It is therefore preferable that the adjustment processing is switchable between the on state and the off state as required.

When performing volume scanning on a site that is not actively moving, it is possible to maintain the time consistency of volume data by having the processing circuitry switch off the adjustment processing.

Note that the operations performed by the processing circuitry 44 after acquisition of the projection data are the same in either of the X-ray CT apparatus 1 and the image generation apparatus 45. Therefore, both the X-ray CT apparatus and the image generation apparatus can obtain the effects of the certain embodiment described above, as well as the effects of the respective modifications described below.

(Modifications)

Examples of modifications of the certain embodiment will each be described.

(First Modification)

Figure 12:
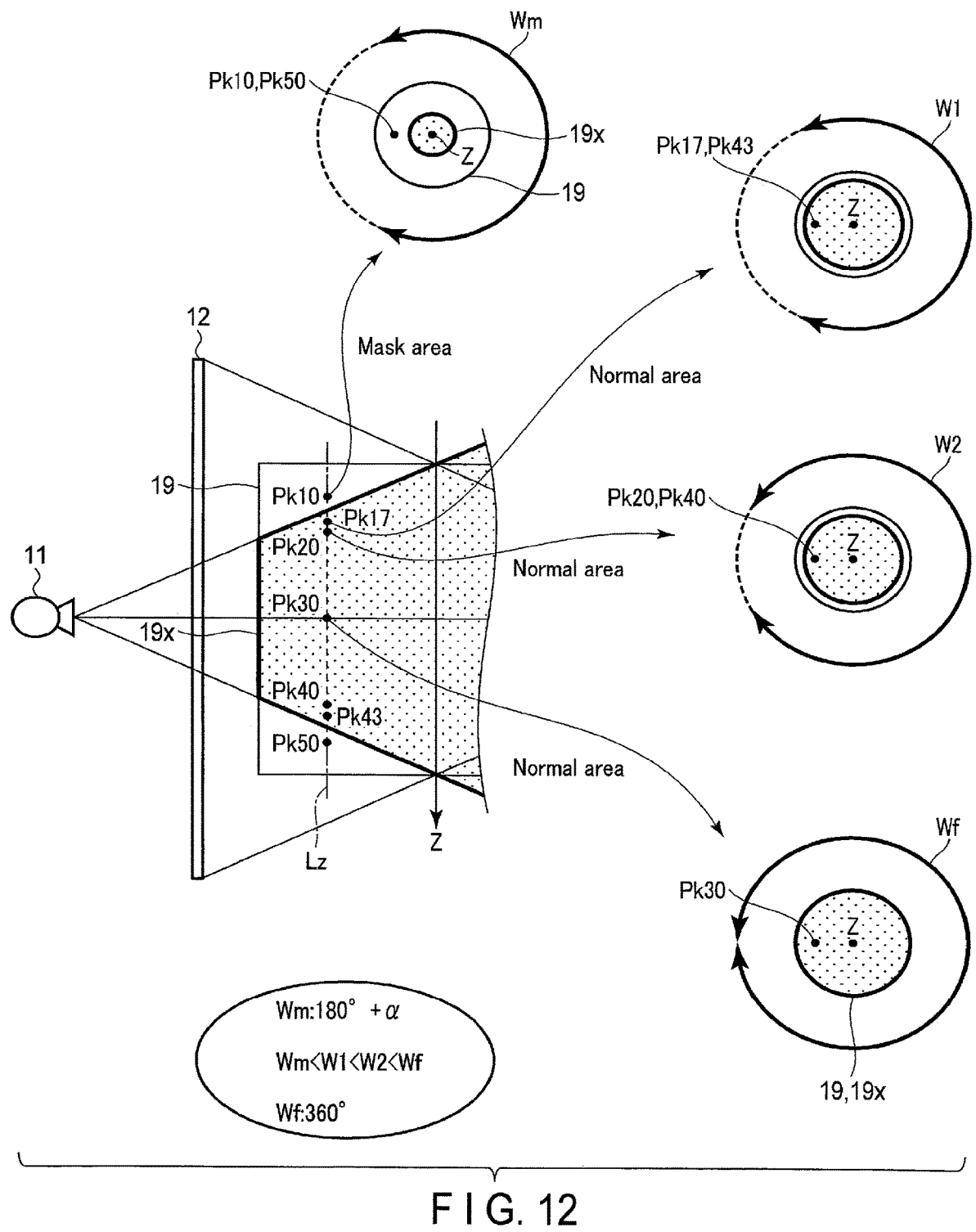
FIG. 12 is a schematic diagram showing adjusted acquisition ranges corresponding to the respective points on a straight line in the context of a first modification of the embodiment.
Figure 13:
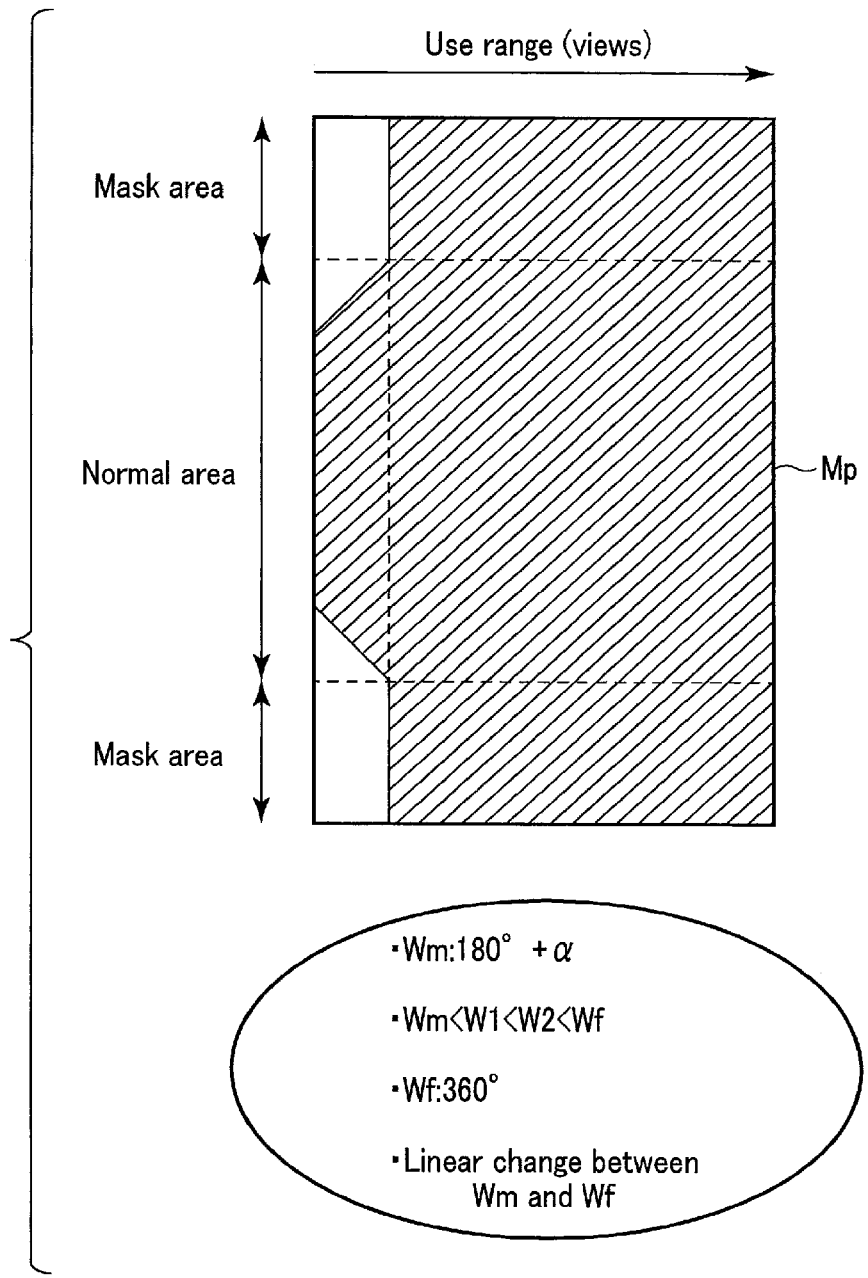
FIG. 13 is a schematic diagram showing one example of projection data maps corresponding to the respective points on the straight line shown in FIG. 12.

The first modification is an example in which the adjustment process by the adjustment function 443 is changed. Specifically, instead of the adjustment process as shown in FIG. 10, the adjustment function 443 adjusts the partial angle (use range) by, as shown in FIGS. 12 and 13, continuously narrowing the acquisition range Wf down to W2, W1, . . . to coincide with the smaller acquisition range Wm, within each partial area in the normal area that involves the boundary with the mask area. In the exemplary projection data map Mp shown in FIG. 13, the continuous narrowing of the acquisition range Wf has been performed linearly. In any case, the first modification can reduce the gap appearing at the boundary between the image of the mask area and the image of the normal area, as in the certain embodiment. Additionally, according to the first modification, the acquisition range Wf is not narrowed down for a center area in the normal area (area portion other than each partial area involving the boundary), and therefore, the image quality of the normal area can be enhanced as compared to the certain embodiment.

(Second Modification)

Figure 14:
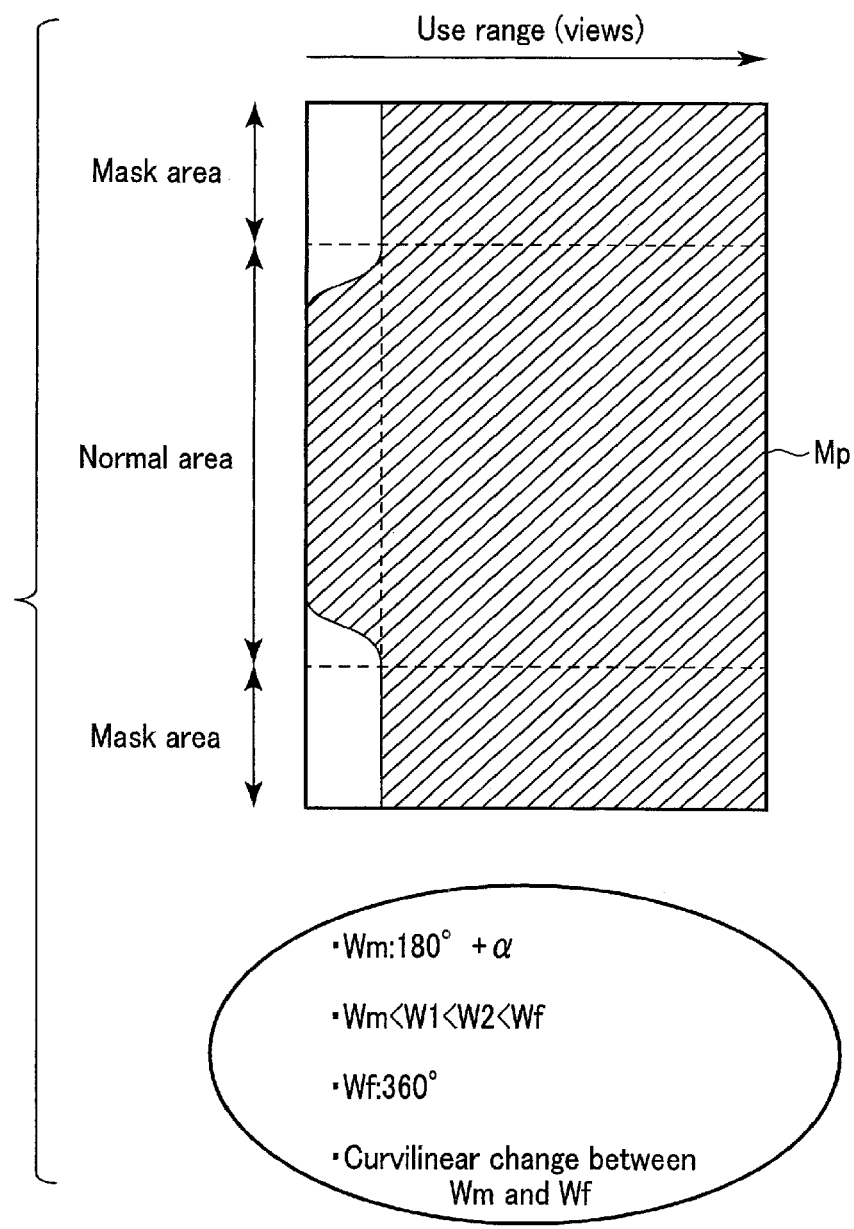
FIG. 14 is a schematic diagram showing one example of projection data maps in the context of a second modification of the embodiment.

The second modification is a modified version of the first modification, and performs the continuous narrowing of the acquisition range Wf curvilinearly. Specifically, FIG. 14 shows one exemplary projection data map Mp of this modification, and as can be seen from this, the adjustment function 443 adjusts the partial angle (the use range) by continuously and curvilinearly narrowing the acquisition range Wf down to W2, W1, . . . to coincide with the smaller acquisition range Wm, within each partial area in the normal area that involves the boundary with the mask area. Adopting this second modification can also provide the same effects as described for the first modification.

(Third Modification)

Figure 15:
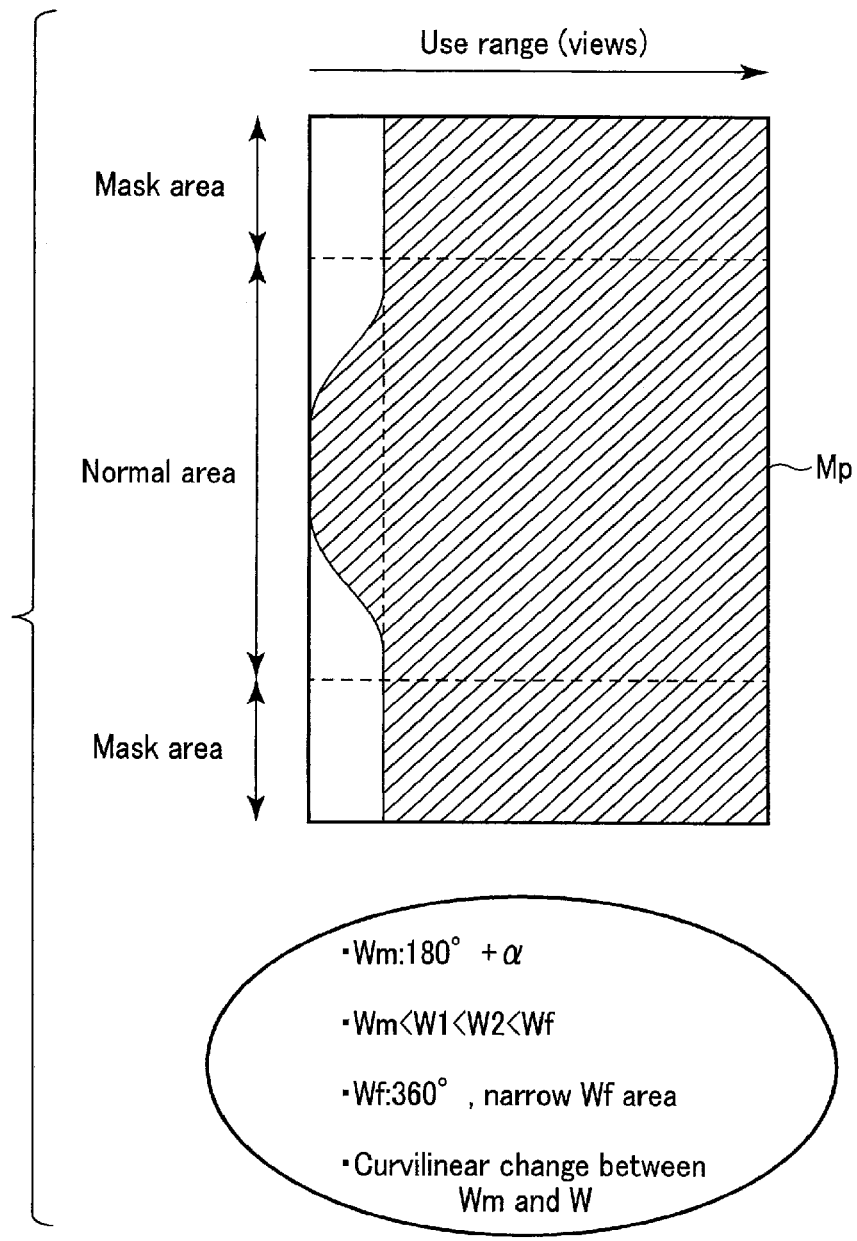
FIG. 15 is a schematic diagram showing one example of projection data maps in the context of a third modification of the embodiment.

The third modification is a modified version of the second modification. Specifically, FIG. 15 shows one exemplary projection data map Mp of this modification, and as can be seen from this, the adjustment function 443 narrows down the center area in the normal area (the area portion other than the partial areas) more than the second modification, when curvilinearly narrowing down the acquisition range Wf within the partial areas. Adopting this third modification can also deliver the same effects as described for the first modification and the second modification. Note, however, that the third modification narrows down the center area (area portion other than the partial areas), and as such, the area for which an image quality can be enhanced is smaller than that in the first modification and the second modification.

(Fourth Modification)

Figure 16:
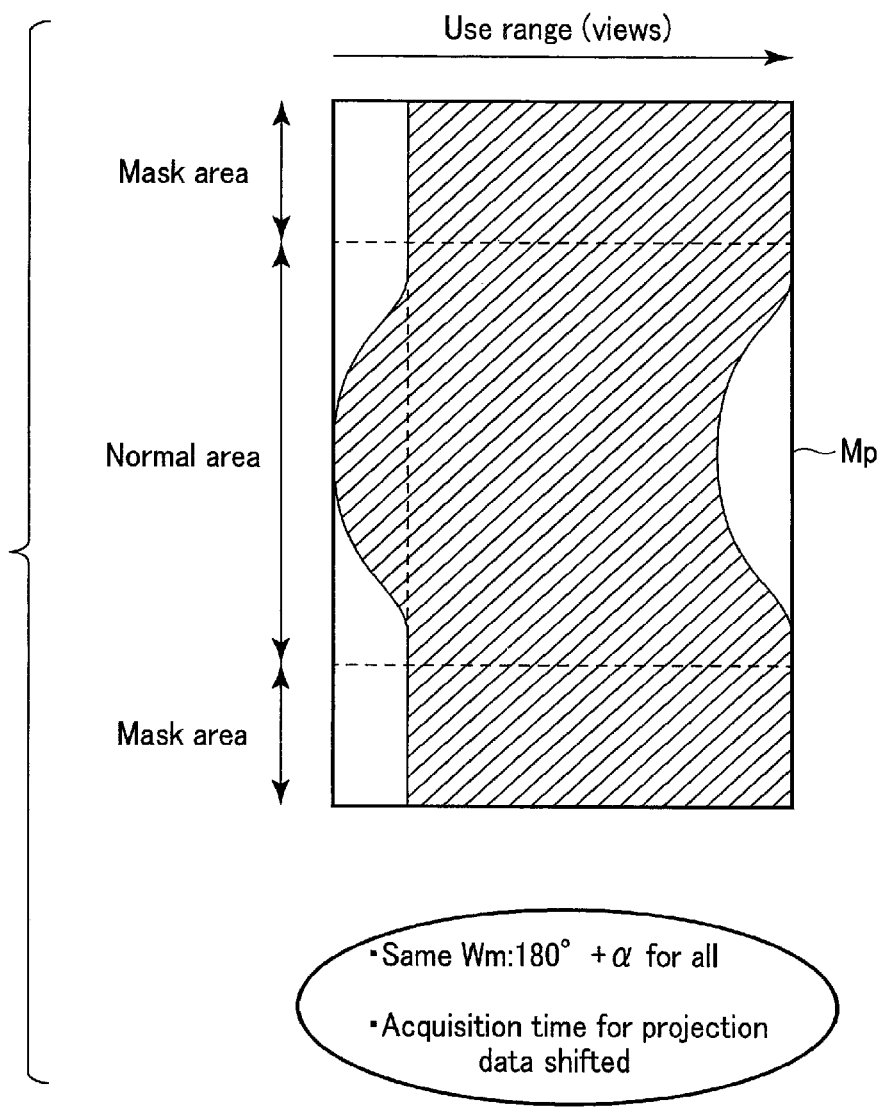
FIG. 16 is a schematic diagram showing one example of projection data maps in the context of a fourth modification of the embodiment.

The fourth modification is a modified version of the certain embodiment. Specifically, FIG. 16 shows one exemplary projection data map Mp of this modification, and as can be seen from this, the adjustment function 443 adjusts the use range used for reconstructing an image of the normal area so that it has the same range as the smaller acquisition range for the mask area and also varies continuously. According to this fourth modification, the same effects as described for the certain embodiment can be obtained, and it is further possible to align the noise appearing on the image of the normal area.

(Fifth Modification)

Figure 17:
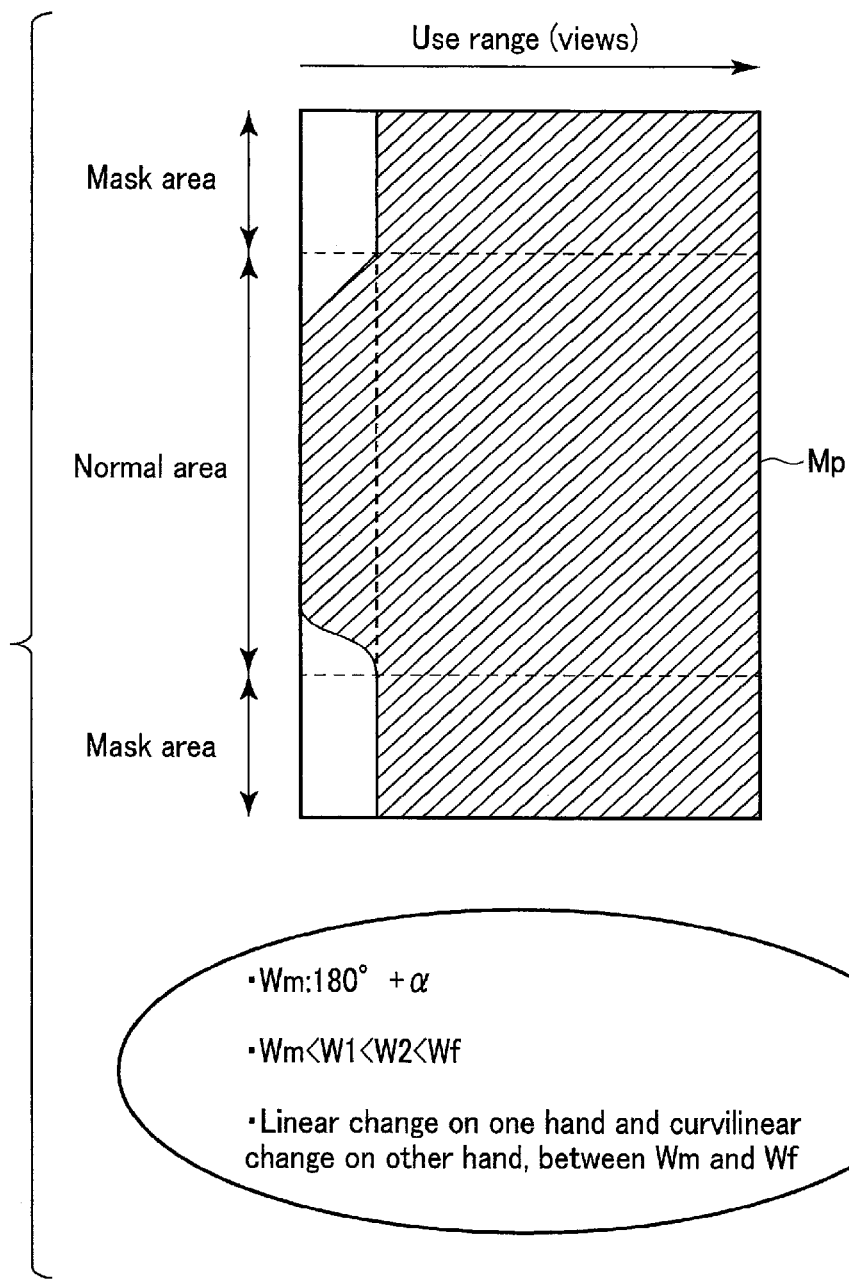
FIG. 17 is a schematic diagram showing one example of projection data maps in the context of a fifth modification of the embodiment.

The fifth modification is a combination of the second modification and the third modification. Specifically, FIG. 17 shows one exemplary projection data map Mp of this modification, and as can be seen from this, the adjustment function 443 continuously and linearly narrows the acquisition range Wf down to W2, W1, . . . to coincide with the smaller acquisition range Wm, within one of the partial areas in the normal area each involving the boundary with the mask area. Also, the adjustment function 443 continuously and curvilinearly narrows the acquisition range Wf down to W2, W1, . . . to coincide with the smaller acquisition range Wm, within the other one of the partial areas. The adjustment function 443 adjusts the use range in this manner.

According to this fifth modification, it is possible to obtain the same effects as described for the second modification and the third modification.

Note that the first to fifth modifications are not intended to be limitative, and the adjustment function 443 according to the certain embodiment may be modified to a configuration to narrow the use range for the normal area down to the use range for the mask area, using a line or a curve having a degree of inclination that would not produce a gap. That is, the use range for the normal area can be continuously or intermittently changed with any given forms, as long as it exists between the one-rotation acquisition range Wf and the mask area acquisition range Wm and its change is within the extent of keeping a gap from appearing at the inter-area positions.

(Sixth Modification)

The sixth modification is for the case of continuously adjusting the use range for the partial area in the normal area, as in the first to fifth modifications, etc., and it adopts a configuration in which the adjustment function 443 adjusts the use range according to user operations. Also, the sixth modification uses the memory 41 that stores multiple projection data maps Mp based on acquired projection data. The projection data maps Mp each indicate the projection data in association with positions on the straight line extending along the rotational axis, and with rotational angles of the X-ray tube 11 that correspond to the acquisition times for the acquisition ranges.

Figure 18:
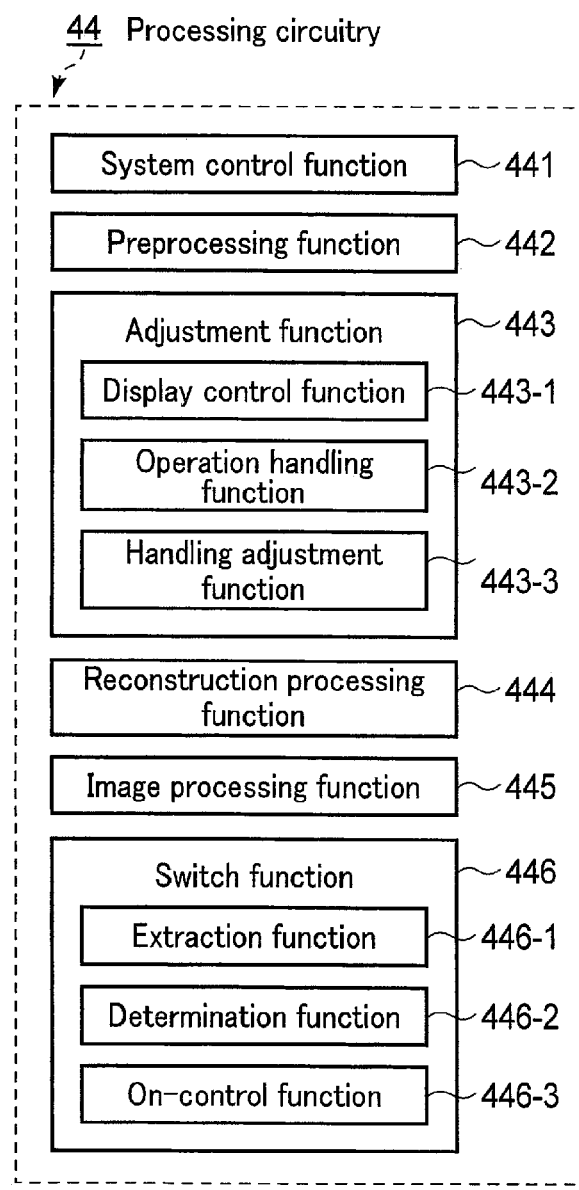
FIG. 18 is a block diagram showing a configuration of processing circuitry for explaining an adjustment function according to a sixth modification of the embodiment.

As shown in FIG. 18, the adjustment function 443 in this modification includes a display control function 443-1, an operation handling function 443-2, and a handling adjustment function 443-3.

The display control function 443-1 controls the display 42 to display one of the multiple projection data maps Mp. The display control function 443-1 additionally controls the display 42 to display the reconstructed image of the normal area and the reconstructed image of the mask area.

The operation handling function 443-2 adjusts, in response to an operation by an operator, the use range (the partial angle of the rotational angles) for the currently-displayed projection data map within its acquisition range.

The handling adjustment function 443-3 adjusts, in accordance with the use range (the partial angle) adjusted by the operation handling function 443-2, the use ranges (the partial angle of the rotational angles) for the projection data maps other than the one currently displayed, within their acquisition ranges.

Accordingly, the reconstruction processing function 444 performs the reconstruction processing based on the multiple projection data maps which each have the use range adjusted by the operation handling function 443-2 or the handling adjustment function 443-3, and obtains the image of the normal area.

The remaining configurations are the same as those described for the certain embodiment.

Figure 19:
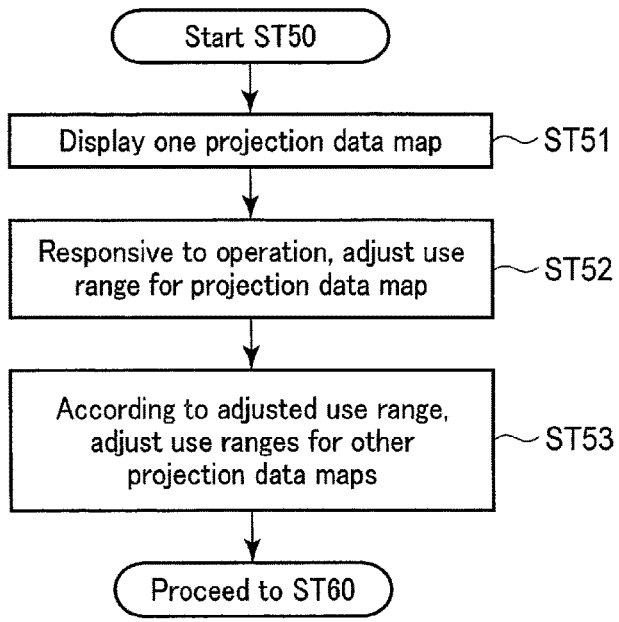
FIG. 19 is a flowchart for explaining operations according to the sixth modification of the embodiment.

Next, the operations in the sixth modification configured as above will be described with reference to the flowcharts of FIGS. 11 and 19.

Figure 11:
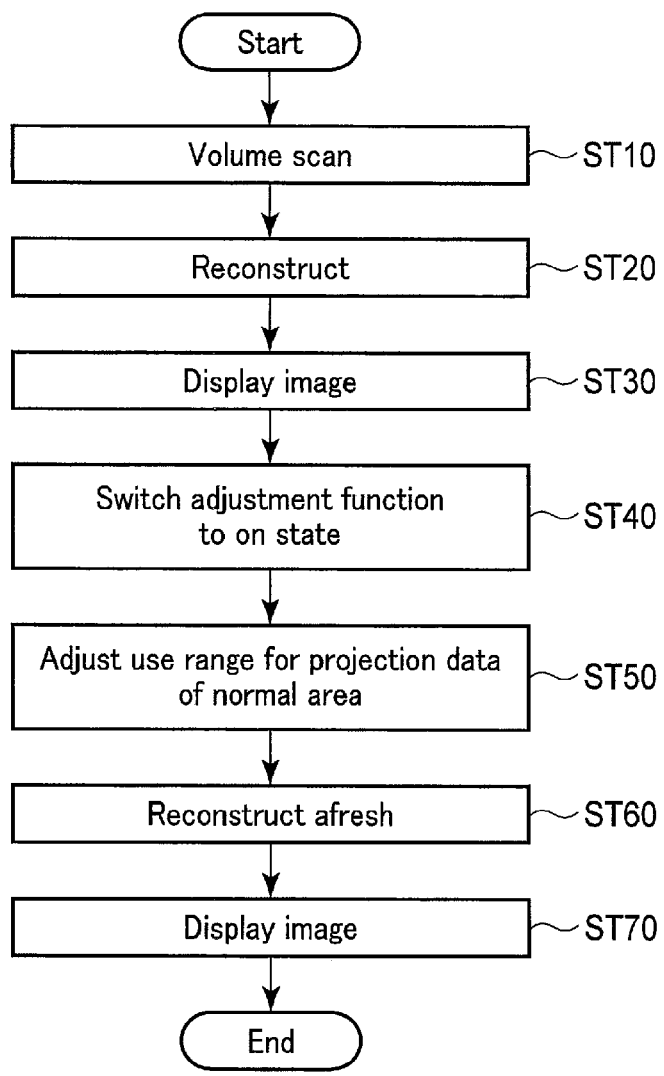
FIG. 11 is a flowchart for explaining operations according to the embodiment.

It will be assumed that steps ST10 to ST40 have been performed in the manner already described using the flowchart of FIG. 11.

Subsequently, the adjustment function 443 adjusts the use range used for reconstructing the image of the normal area, within the acquisition range Wf for the projection data of the normal area (step ST50). Unlike in the certain embodiment, the adjustment function 443 adjusts the use range by continuously narrowing the acquisition range Wf down to W2, W1, . . . to coincide with the smaller acquisition range Wm, within the partial area in the normal area that involves the boundary with the mask area. This step ST50 is performed as shown in FIG. 19.

That is, the display control function 443-1 controls the display 42 to display one of the multiple projection data maps Mp (step ST51). For example, an instance will be supposed where an operator's operation has designated, through the input interface 43, a pixel within the region of interest (ROI) in the image that is currently displayed in accordance with step ST30. At this time, the display control function 443-1 controls the display 42 to display the projection data map Mp corresponding to the straight line Lz covering the designated pixel.

Then, the operation handling function 443-2 adjusts, in response to the operator's operation through the input interface 43, the use range for the currently-displayed projection data map Mp, within its acquisition range (step ST52).

The handling adjustment function 443-3 adjusts, in accordance with the use range adjusted by the operation handling function 443-2, the use ranges for the projection data maps other than the currently-displayed projection data map Mp, within their acquisition ranges (step ST53). Thereafter, the reconstruction processing function 444 reconstructs the image of the normal area based on the multiple projection data maps each having the adjusted use range (step ST60).

The display control function 443-1 controls the display 42 to display the reconstructed image of the normal area and the reconstructed image of the mask area (step ST70). If there is a gap between the displayed images of the normal area and the mask area, the processing steps ST52 to ST70 are repeated again upon an operation from the operator.

Thus, according to the sixth embodiment adopting the configuration to adjust the use range for the normal area in response to an operator's operation, the same effects as described for the first modification to the fifth modification can be obtained, and it is further possible to adjust the image quality as desired according to operations by the operator.

Also, in accordance with the use range adjusted by the operation handling function 443-2, the use ranges for the projection data maps other than the currently-displayed projection data map are adjusted within their acquisition ranges. Therefore, the adjustment operations can be performed smoothly as compared to the cases of an operator adjusting all the projection data maps.

(Seventh Modification)

The seventh modification is a modified version of each of the certain embodiment and the first to fifth modifications, and it is a concrete example for realizing the switch function 446 with an automatic configuration. With the automatic configuration, for example, the processing circuitry 44 implementing the switch function 446 switches the adjustment function 443 from the off state to the on state in response to images of the normal area and the mask area being obtained by the reconstruction processing, and based on a gap between the obtained images.

The switch function 446 as above includes, for example, an extraction function 446-1, a determination function 446-2, and an on-control function 446-3.

The extraction function 446-1 extracts an edge of the image of the normal area. For the edge extraction processing, the known image processing techniques may be discretionarily adopted. Also, for easy distinction between an edge and noise, the edge extraction processing should preferably utilize the edge directions (circumferential direction, oblique direction, etc.) according to the image section (axial plane, coronal plane, sagittal plane, etc.). Furthermore, for accelerated processing, the edge extraction processing should preferably extract an edge from, for example, the area designated by the operation on the input interface 43.

The determination function 446-2 determines, based on the result of this edge extraction, the size of the gap appearing between the images obtained by the reconstruction processing.

The on-control function 446-3 switches on the adjustment function 443 (adjustment processing) if the result of the determination by the determination function 446-2 indicates that the gap is large.

The remaining configurations are the same as those described for the certain embodiment and the first to fifth modifications, respectively.

Figure 20:
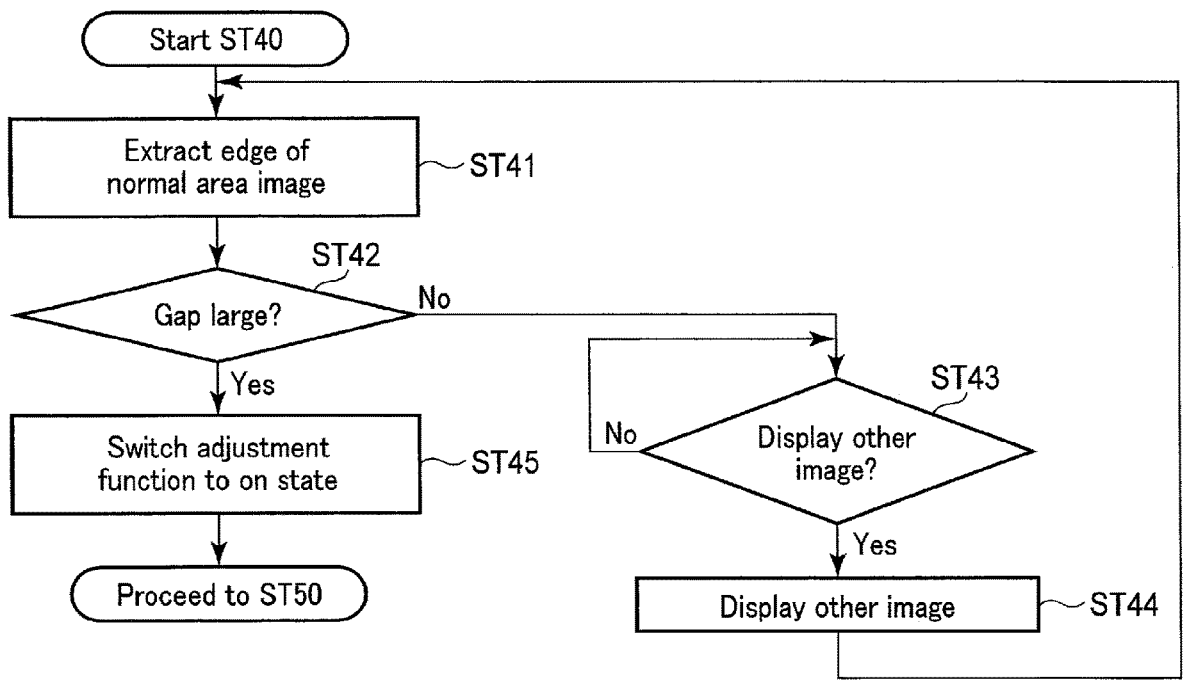
FIG. 20 is a flowchart for explaining operations according to a seventh modification of the embodiment.

Next, the operations in the seventh modification configured as above will be described with reference to the flowcharts of FIGS. 11 and 20.

It will be assumed that steps ST10 to ST30 have been performed in the manner already described using the flowchart of FIG. 11. Also, the description will assume that, upon these steps, the images of the normal area and the mask area are obtained through the reconstruction processing and displayed, and there is a gap appearing at the boundary between the images.

Subsequently, the switch function 446 switches the adjustment function 443 to the on state (step ST40). Unlike in the certain embodiment, the switch function 446 switches on the adjustment function 443 based on the gap between the obtained images. This step ST40 is performed as shown in FIG. 20.

First, the extraction function 446-1 extracts an edge of the image of the normal area (step ST41).

The determination function 446-2 determines, based on the result of this edge extraction, the size of the gap between the obtained images (step ST42). If the gap is smaller than a threshold, display of the current images is continued until other images (a reconstructed image) are displayed (step ST43). When other images are displayed (step ST44) after step ST43, the operation flow returns to step ST41.

On the other hand, if the result of the determination in step ST42 indicates that the gap is large, the on-control function 446-3 switches on the adjustment function 443 (adjustment processing) (step ST45).

Thereafter, steps ST50 to ST70 are performed in the manner already described using the flowchart of FIG. 11.

As such, according to the seventh modification, the adjustment function 443 is switched to the on state based on the gap between the images obtained by the reconstruction processing. Therefore, the same effects as described respectively for the certain embodiment and the first to fifth modifications can be obtained, and it is further possible to save the work needing to be done by an operator manipulating the switch function 446.

Also, according to the seventh modification, an edge of the image of the normal area is extracted, the size of the gap between the images obtained by the reconstruction processing is determined based on the result of the edge extraction, and the adjustment function is switched on in response to the gap being large. With this, the seventh modification can be readily realized using the existing edge extraction technique.

Furthermore, according to the seventh modification that adopts the configuration of switching on the adjustment function 443 of each of the certain embodiment and the first to fifth modifications, the use range for the normal area can be automatically adjusted. Nevertheless, the seventh modification can be combined with the sixth modification that is related to manual adjustment of the use ranges.

(Eighth Modification)

The eighth modification is a modified version of the seventh modification, and it is another concrete example for realizing the switch function 446 with an automatic configuration. Specifically, the eighth modification realizes the automatic switch function 446 as in the following mode (a), (b), or (c).

(a) Mode to control the adjustment function 443 to be the on state for the whole of a four-dimensional image.

(b) Mode to control the adjustment function 443 to be the off state for the whole of a four-dimensional image.

(c) Mode to control the adjustment function 443 to be the on state for particular time phases among the whole of a four-dimensional image, and to control the adjustment function 443 to be the off state for time phases which are different from the particular time phases among the four-dimensional image.

The mode (a) or (b) is used when the four-dimensional image is, for example, scheduled to undergo a postprocessing application for analysis, such as a dynamic state analysis, in order to enhance noise uniformity. The presence of such a schedule can be determined according to, for example, whether or not any postprocessing application has been set prior to the four-dimensional scanning operation for acquiring the four-dimensional image. The mode (a) is used when one or more gaps in the four-dimensional image are equal to or greater than a threshold. The mode (b) is used when the gaps in the four-dimensional image are all below the threshold.

The mode (c) is used when the four-dimensional image is not scheduled to undergo a postprocessing application for analysis. The particular time phases referred to in the mode (c) may be the time phases of the four-dimensional image that include a time phase at which the gap is equal to or greater than the threshold, and the time phases before and after this time phase.

Accordingly, the memory 41 is set with the schedule for executing a postprocessing program for analysis based on an operator's operation for the image obtained by the processing circuitry 44. The schedule in this context may not have to contain date and time information. For example, the purpose would be served if the schedule contains some type of schedule-related information, such as identification information of the postprocessing program (e.g., name), and condition information indicative of expected postprocessing for analysis.

In the switch function 446, for example, the on-control function 446-3 described above realizes the following functions. The on-control function 446-3 determines whether or not the schedule has been set. If, as a result, it is determined that the schedule has been set, the on-control function 446-3 switches the adjustment processing for the partial-angle adjustment to an always-on state or to an always-off state, according to the size of the gap between the images of the first area and the second area. Also, if it is determined that the schedule has not been set, the on-control function 446-3 switches this adjustment processing to the on state for each of the particular time phases corresponding to the case of having a gap larger than the threshold.

The remaining configurations are the same as those described for the seventh modification.

Figure 21:
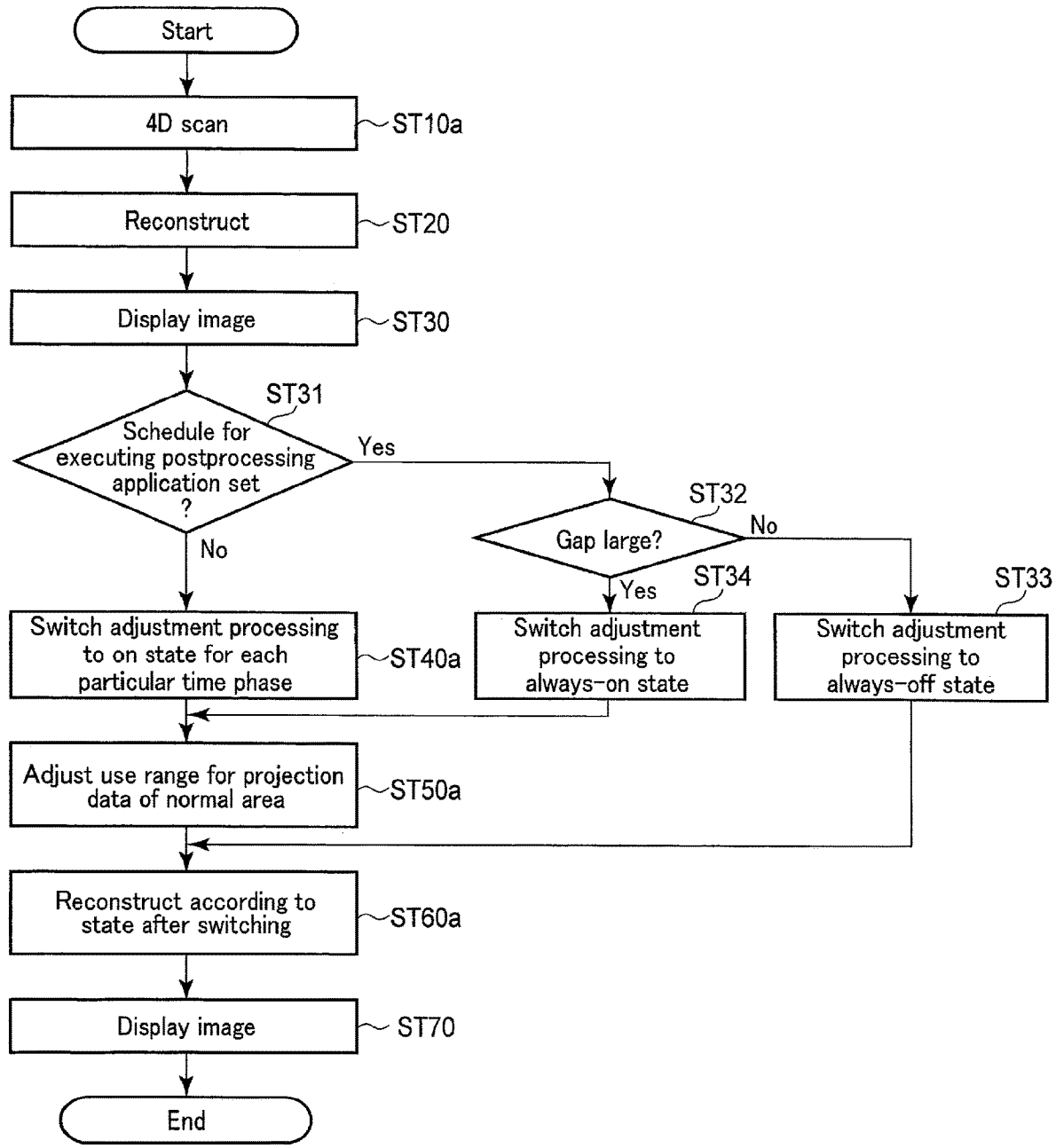
FIG. 21 is a flowchart for explaining operations according to an eighth modification of the embodiment.

Next, the operations in the eighth modification configured as above will be described with reference to the flowchart of FIG. 21. The description will focus on the operations after completion of the tasks, such as positioning by scanogram imaging, setting of imaging conditions, setting of a schedule for executing a postprocessing application for analysis, and activation of gantry rotation. Note that the setting of a schedule for executing a postprocessing application for analysis is omitted when there is no such schedule. Also, the description will assume an instance where the adjustment function 443 is in the off state at the start of step ST10a.

Now, the X-ray CT apparatus 1 performs four-dimensional scanning for a subject by continuously conducting the volume scanning as described for step ST10 above (step ST10a). Based on the result of performing the four-dimensional scanning, steps ST20 to ST30 are performed as already described.

Next, the processing circuitry 44 performs the on-control function 446-3 in the switch function 446. At this time, the processing circuitry 44 determines whether or not a schedule for executing a postprocessing program for analysis has been set to the memory 41 for the image obtained by the four-dimensional scanning (step ST31).

If, as a result of step ST31, it is determined that the schedule has been set, the processing circuitry 44 switches the adjustment processing for the partial-angle adjustment to the always-on state or to the always-off state, according to the size of the gap between the images of the first area and the second area (steps ST32 to ST34). More specifically, and for example, the size of the gap is determined in a manner similar to steps ST41 to ST42 described above (step ST32), and if the gap is determined to be below the threshold, the adjustment processing is switched to the always-off state (step ST33), and the operation transitions to step ST60a. If the determination in step ST32 indicates that the gap is large, the adjustment processing is switched to the always-on state (step ST34), and the operation transitions to step ST50a.

On the other hand, if, as a result of step ST31, it is determined that the schedule has not been set, the adjustment processing is switched to the on state for each of the particular time phases corresponding to the case of having a gap larger than the threshold (step ST40a).

In step ST50a, which is after step ST40a or step ST34, the processing circuitry 44 adjusts the use range used for reconstructing the image of the normal area within the acquisition range Wf for the projection data of the normal area, in a manner similar to step ST50 described above, provided that the adjustment processing is in the on state.

In step ST60a, which is after step ST50a or step ST33, the processing circuitry 44 performs the reconstruction processing according to the post-switching on/off state of the adjustment processing. More specifically, as an example, the processing circuitry 44 reconstructs the image of the normal area using the projection data from the use range according to such an on/off state, and also reconstructs the image of the mask area using the projection data from the smaller acquisition range. Note that the use range according to the on state has been adjusted. The use range according to the off state has not been adjusted.

Thereafter, the image processing function 445 converts the images reconstructed in step ST60a into tomographic data of a given section, three-dimensional image data, etc. The tomographic data, the three-dimensional image data, etc., after the conversion are displayed by the display 42 (step ST70).

According to the eighth modification described, the memory is set with a schedule for executing a postprocessing program for analysis of the obtained image, based on an operation by an operator. The processing circuitry determines whether or not the schedule has been set, and if the determination result indicates that the schedule has been set, it switches the adjustment processing for the partial-angle adjustment to either an always-on state or an always-off state, according to the size of a gap between the images of the first area and the second area. Also, if the determination result indicates that the schedule has not been set, the processing circuitry switches the adjustment processing to the on state for each of the particular time phases corresponding to the case of having a gap larger than the threshold.

In this manner, if there is a schedule for executing a postprocessing program for analysis, the adjustment processing is switched to the always-on state or always-off state. For example, if there is even one large gap within a four-dimensional image, the adjustment processing is switched to the always-on state. Also, if there is not any gap within a four-dimensional image, the adjustment processing is switched to the always-off state. Accordingly, with the configuration of controlling the adjustment processing to be always in the same state, the same effects as described for the certain embodiment can be obtained, and it is further possible to eliminate the noise variation that could accompany the switching of the adjustment processing so that the noise uniformity can be enhanced. Consequently, the analysis result by the postprocessing can be expected to have a higher reliability.

Also, with the configuration of switching the adjustment processing to the on state for each of the particular time phases (where a gap would appear due to four-dimensional scanning) when there is no schedule for executing a postprocessing program for analysis, it is possible to proceed with the reconstruction operation while avoiding the gaps appearing in the respective particular time phases.

(Ninth Modification)

The ninth modification is a modified version of each of the certain embodiment and the first to eighth modifications, and it is a concrete example for generating the projection data map Mp based on power-coordinate system. Note, however, that the following description will basically assume that this modification is applied to the first to third modifications and the fifth to eighth modifications, corresponding to the cases of continuously narrowing down the acquisition range Wf for the normal area to coincide with the smaller acquisition range Wm for the mask area.

It will be supposed that, as shown in FIG. 22, there is a point Pk (r, θ) in a mask area on the axial plane, where the mask area is located on the outer peripheral side of a normal area. The point Pk (r, θ) is defined by the polar coordinates of a given radius r from the rotational axis Z and an angle θ with respect to the horizontal axis X. In this instance, the point Pk (r, θ) corresponds to the position on the circumference of a circle Lθ centering on the rotational axis Z and having the given radius r. Also, the angular position (θ) corresponding to the point Pk in the mask area and the angular position (θ+180°) corresponding to the midpoint of the acquisition range Wm are in the relationship whereby they are opposed to each other with the rotational axis Z therebetween. The point Pk corresponds to a target pixel when an image is displayed.

Figure 23:
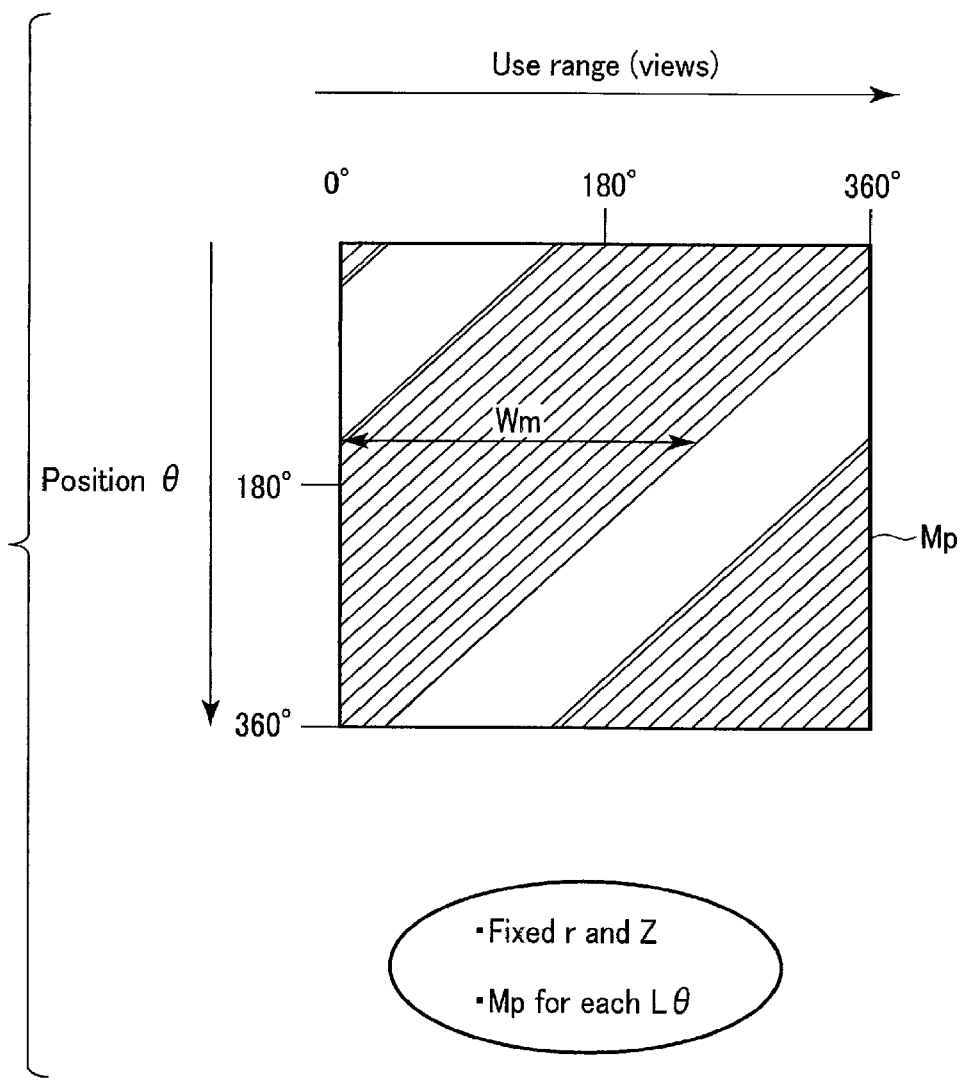
FIG. 23 is a schematic diagram showing one example of projection data maps in the context of the ninth modification of the embodiment.

The detection data (projection data) for such a point Pk on the circle Lθ is stored in the memory 41 in the form of a projection data map Mp as shown in FIG. 23, in which the radius r and the position in the direction of the rotational axis Z are fixed. Assuming that the vertical axis represents the position of each point Pk on the circle Lθ and the horizontal axis represents views (view numbers), this projection data map Mp plots the digital value of the X-ray intensity for the point Pk at the intersection between the vertical axis and the horizontal axis. The range of views, for which the digital values of x-ray intensities are plotted for the position of a given point Pk, conforms to the use range Wm corresponding to the point Pk. The use range corresponding to the point Pk in the mask area is 180°+α, and the midpoint of the use range Wm moves to a position which is opposed to the position (θ) of the point Pk according to the same (θ). Such a projection data map Mp is stored in the memory 41 for each circle Lθ. Note that the preprocessing function 442 generates a multiple of such projection data maps Mp based on, for example, projection data before the preprocessing, and writes these projection data maps Mp in the memory 41. The projection data maps Mp are each indicative of the projection data in association with the position on the circumference of the circle Lθ centering on the rotational axis Z and having a given radius r (a position on the mask area or the normal area), and with the use range (the view number). In the example described, the views on the horizontal axis in the projection data map Mp represent the rotational angle of the X-ray tube 11, and the range of the views corresponds to the acquisition range or the use range. The horizontal axis in the projection data map Mp may represent the acquisition times or view numbers for the acquisition ranges Wf and Wm.

Now, it will be supposed that, as shown on the left side of FIG. 24, a point Pk1 (r1, θ) in the mask area, a point Pk2 (r2, θ) in the partial area in the normal area that involves the boundary with the mask area, and a point Pk3 (r3, θ) in the normal area other than the partial area are given, using three radius values r1, r2, and r3 (where r3<r2<r1) with a constant Z-coordinate value and a given angle θ.

In this instance, for the point Pk1 in the mask area, the use range Wm according to the position (θ) of the point Pk1 is indicated by the projection data map Mp as shown in the upper right portion of FIG. 24, which is similar to FIG. 23.

For the point Pk2 in the partial area, the use range W1 (>Wm) according to the position (θ) of the point Pk2 is indicated by the projection data map Mp as shown in the middle right portion of FIG. 24. Note that the use range W1 according to the position (θ) of the point Pk2 is a range that has been narrowed from the acquisition range Wf for the normal area to approach the use range Wm for the mask area (Wf>W1>Wm).

For the point Pk3 in the normal area other than the partial area, the use range Wf (=360°) according to the position (θ) of the point Pk3 is indicated by the projection data map Mp as shown in the lower right portion of FIG. 24. Note that, when this modification is applied to the certain embodiment and the fourth modification, where the acquisition range Wf for the normal area is adjusted to coincide with the smaller acquisition range Wm for the mask area, the use ranges W1 and Wf indicated in the respective projection data maps Mp in the middle-right portion and the lower-right portion of FIG. 24 may be adjusted to have the same range as the acquisition range Wm indicated in the projection data map Mp in the upper right portion of the figure. Also, for application to the fourth modification, the use range adjusted to have the same range may further be moved.

The configurations and operations, other than the projection data maps Mp, are the same as those described for each of the certain embodiment and the first to eighth modifications, to which this modification is intended to be applied.

According to the ninth modification described, the same effects as described respectively for the certain embodiment and the first to eighth modifications can be obtained from the configuration of adopting the positions on the circles each centering on the rotational axis and having a given radius r, instead of adopting the positions on the straight line extending along the rotational axis.

According to at least one of the certain embodiment and the modifications described, the data acquisition circuitry acquires projection data of a first area and projection data of a second area via the X-ray detector, in conjunction with the X-ray generator rotating around a subject once. The first area is an area where the complete projection data for this one rotation is obtained. The second area is an area located on both sides of the first area in the direction along the rotational axis of the X-ray generator, and where the projection data for only an angle smaller than one rotation can be obtained. The processing circuitry obtains images by performing, for at least part of the first area, reconstruction processing using the projection data corresponding to a partial angle among the projection data available for reconstruction and by performing, for the second area, reconstruction processing using the projection data of the acquisition range smaller than one rotation.

Therefore, it is possible to reduce the gap appearing at the boundary between the image of the mask area (second area) and the image of the normal area (first area) when an actively moving site is subject to volume scanning.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
an X-ray generator configured to generate a cone-beam X-ray;
an X-ray detector configured to detect the X-ray from the X-ray generator through a subject;
data acquisition circuitry configured to acquire projection data of a first area and projection data of a second area via the X-ray detector in conjunction with the X-ray generator performing one rotation around the subject, the first area being an area where the projection data is complete for the one rotation, the second area being an area located on both sides of the first area in a direction along a rotational axis of the X-ray generator and where the projection data is obtained for an angle smaller than the one rotation; and
processing circuitry configured to perform, for at least part of the first area, reconstruction processing using the projection data corresponding to a partial angle among the projection data available for reconstruction and to perform, for the second area, reconstruction processing using the projection data of a smaller acquisition range that is smaller than the one rotation, so that an image of the first area and an image of the second area are obtained, wherein the processing circuitry is configured to adjust the partial angle by continuously narrowing down an acquisition range for a partial area to coincide with the smaller acquisition range, the partial area being within the first area and involving a boundary with the second area,
the X-ray computed tomography apparatus further comprising a memory configured to store a plurality of projection data maps based on the acquired projection data, the projection data maps each indicative of the projection data in association with a position on a line extending along the rotational axis of the X-ray generator and with a rotational angle of the X-ray generator that correspond to an acquisition time for the acquisition range, wherein the processing circuitry is configured to
control a display to display one of the projection data maps,
adjust, in response to an operator's operation, a partial angle of the rotational angle for the displayed one of the projection data maps within its acquisition range,
adjust, in accordance with the partial angle adjusted in response to the operator's operation, partial angles of the rotational angle for the projection data maps other than the displayed one within their acquisition ranges,
perform the reconstruction processing based on the projection data maps each having the adjusted partial angle to obtain the image of the first area, and
control the display to display the obtained images of the first area and the second area.

2. The X-ray computed tomography apparatus according to claim 1, wherein the processing circuitry is configured to switch the adjustment processing from the off state to the on state in response to the reconstruction processing obtaining the images of the first area and the second area and based on a gap between the obtained images.

3. The X-ray computed tomography apparatus according to claim 2, wherein the processing circuitry is configured to
extract an edge of the image of the first area,
determine a size of the gap based on a result of extracting the edge, and
switch, if the size of the gap is determined to be large, the adjustment processing to the on state.

4. The X-ray computed tomography apparatus according to claim 1, further comprising a memory configured to be set with, in response to an operator's operation, a schedule for executing a post-processing program for analysis for the obtained images,
wherein the processing circuitry is configured to
determine whether or not the schedule is set,
switch, if the schedule is determined to be set, adjustment processing for adjusting the partial angle to an always-on state or an always-off state, according to a size of a gap between the images of the first area and the second area, and
switch, if the schedule is not determined to be set, the adjustment processing to an on state for each time phase corresponding to the gap being larger than a threshold.

5. The X-ray computed tomography apparatus according to claim 1, wherein the processing circuitry is configured to use the projection data corresponding to the partial angle for keeping continuity near a boundary between the first area and the second area.

6. An X-ray computed tomography apparatus comprising:
an X-ray generator configured to generate a cone-beam X-ray;
an X-ray detector configured to detect the X-ray from the X-ray generator through a subject;
data acquisition circuitry configured to acquire projection data of a first area and projection data of a second area via the X-ray detector in conjunction with the X-ray generator performing one rotation around the subject, the first area being an area where the projection data is complete for the one rotation, the second area being an area located on both sides of the first area in a direction along a rotational axis of the X-ray generator and where the projection data is obtained for an angle smaller than the one rotation; and
processing circuitry configured to perform, for at least part of the first area, reconstruction processing using the projection data corresponding to a partial angle among the projection data available for reconstruction and to perform, for the second area, reconstruction processing using the projection data of a smaller acquisition range that is smaller than the one rotation, so that an image of the first area and an image of the second area are obtained, wherein the processing circuitry is configured to adjust the partial angle by continuously narrowing down an acquisition range for a partial area to coincide with the smaller acquisition range, the partial area being within the first area and involving a boundary with the second area,
the X-ray computed tomography apparatus further comprising a memory configured to store a plurality of projection data maps based on the acquired projection data, the projection data maps each indicative of the projection data in association with a position on a circumference of a circle centering on the rotational axis of the X-ray generator and having a predetermined radius and with a rotational angle of the X-ray generator that correspond to an acquisition time for the acquisition range,
wherein the processing circuitry is configured to
control a display to display one of the projection data maps,
adjust, in response to an operator's operation, a partial angle of the rotational angle for the displayed one of the projection data maps within its acquisition range,
adjust, in accordance with the partial angle adjusted in response to the operator's operation, partial angles of the rotational angle for the projection data maps other than the displayed one within their acquisition ranges,
perform the reconstruction processing based on the projection data maps each having the adjusted partial angle to obtain the image of the first area, and
control the display to display the obtained images of the first area and the second area.

7. The X-ray computed tomography apparatus according to claim 6, wherein the processing circuitry is configured to use the projection data corresponding to the partial angle for keeping continuity near a boundary between the first area and the second area.

8. An X-ray computed tomography apparatus comprising:
an X-ray generator configured to generate a cone-beam X-ray;
an X-ray detector configured to detect the X-ray from the X-ray generator through a subject;
data acquisition circuitry configured to acquire projection data of a first area and projection data of a second area via the X-ray detector in conjunction with the X-ray generator performing one rotation around the subject, the first area being an area where the projection data is complete for the one rotation, the second area being an area located on both sides of the first area in a direction along a rotational axis of the X-ray generator and where the projection data is obtained for an angle smaller than the one rotation; and
processing circuitry configured to perform, for at least part of the first area, reconstruction processing using the projection data corresponding to a partial angle among the projection data available for reconstruction and to perform, for the second area, reconstruction processing using the projection data of a smaller acquisition range that is smaller than the one rotation, so that an image of the first area and an image of the second area are obtained, wherein the processing circuitry is configured to switch adjustment processing for adjusting the partial angle between an on state and an off state in response to an operator's operation.

9. The X-ray computed tomography apparatus according to claim 8, wherein the processing circuitry is configured to switch the adjustment processing from the off state to the on state in response to the reconstruction processing obtaining the images of the first area and the second area and based on a gap between the obtained images.

10. The X-ray computed tomography apparatus according to claim 9, wherein
the processing circuitry is configured to
extract an edge of the image of the first area,
determine a size of the gap based on a result of extracting the edge, and
switch, if the size of the gap is determined to be large, the adjustment processing to the on state.

11. An X-ray computed tomography apparatus comprising:
an X-ray generator configured to generate a cone-beam X-ray;
an X-ray detector configured to detect the X-ray from the X-ray generator through a subject;
data acquisition circuitry configured to acquire projection data of a first area and projection data of a second area via the X-ray detector in conjunction with the X-ray generator performing one rotation around the subject, the first area being an area where the projection data is complete for the one rotation, the second area being an area located on both sides of the first area in a direction along a rotational axis of the X-ray generator and where the projection data is obtained for an angle smaller than the one rotation; and
processing circuitry configured to perform, for at least part of the first area, reconstruction processing using the projection data corresponding to a partial angle among the projection data available for reconstruction and to perform, for the second area, reconstruction processing using the projection data of a smaller acquisition range that is smaller than the one rotation, so that an image of the first area and an image of the second area are obtained,
the X-ray computed tomography apparatus further comprising a memory configured to be set with, in response to an operator's operation, a schedule for executing a post-processing program for analysis for the obtained images,
wherein the processing circuitry is configured to
determine whether or not the schedule is set,
switch, if the schedule is determined to be set, adjustment processing for adjusting the partial angle to an always-on state or an always-off state, according to a size of a gap between the images of the first area and the second area, and
switch, if the schedule is not determined to be set, the adjustment processing to an on state for each time phase corresponding to the gap being larger than a threshold.

* * * * *